(12) United States Patent
Tyber et al.

(10) Patent No.: US 8,343,199 B2
(45) Date of Patent: Jan. 1, 2013

(54) INTRAMEDULLARY FIXATION SCREW, A FIXATION SYSTEM, AND METHOD OF FIXATION OF THE SUBTALAR JOINT

(75) Inventors: Jeff Tyber, Bethlehem, PA (US); Jamy Gannoe, West Milford, NJ (US); Adam Mantzaris, Hoboken, NJ (US); Selene Parekh, Cary, NC (US)

(73) Assignee: Extremity Medical, LLC, Parsippany, NJ (US)

( * ) Notice: Subject to any disclaimer, the term of this patent is extended or adjusted under 35 U.S.C. 154(b) by 0 days.

(21) Appl. No.: 12/874,801

(22) Filed: Sep. 2, 2010

(65) Prior Publication Data

US 2011/0213367 A1    Sep. 1, 2011

Related U.S. Application Data

(63) Continuation-in-part of application No. 12/658,680, filed on Feb. 11, 2010, which is a continuation-in-part of application No. 12/456,808, filed on Jun. 23, 2009.

(60) Provisional application No. 61/132,932, filed on Jun. 24, 2008.

(51) Int. Cl.
*A61B 17/04* (2006.01)
*A61B 17/56* (2006.01)

(52) U.S. Cl. .............. 606/301; 606/72; 606/62

(58) Field of Classification Search .................. 606/96
See application file for complete search history.

(56) References Cited

U.S. PATENT DOCUMENTS

| | | | |
|---|---|---|---|
| 928,997 A | 7/1909 | Muller | |
| 2,398,220 A | 4/1946 | Gelpcke | |
| 2,580,821 A | 1/1952 | Nicola | |
| 3,019,686 A | 2/1962 | Behrle | |
| 3,200,694 A | 8/1965 | Rapata | |
| 3,411,398 A | 11/1968 | Blakeley et al. | |
| 3,474,537 A | 10/1969 | Christensen | |
| 3,924,276 A | 12/1975 | Eaton | |
| 4,152,533 A | 5/1979 | Gazda | |
| 4,381,770 A | 5/1983 | Neufeld | |
| 4,465,065 A | 8/1984 | Gotfried et al. | |
| 4,760,843 A | 8/1988 | Fischer et al. | |
| 4,795,294 A | 1/1989 | Takada et al. | |
| 4,854,797 A | 8/1989 | Gourd | |
| 4,930,963 A | 6/1990 | Rockenfeller et al. | |
| 4,940,467 A | 7/1990 | Tronzo | |
| 4,947,502 A | 8/1990 | Engelhardt | |

(Continued)

FOREIGN PATENT DOCUMENTS

WO    WO 2006116164    11/2006

(Continued)

*Primary Examiner* — Alvin Stewart
*Assistant Examiner* — Stuart S Bray
(74) *Attorney, Agent, or Firm* — Ward & Zinna, LLC

(57) ABSTRACT

An intramedullary screw and fixation system for intraosseous bone fusion of the subtalar joint includes a lag screw member, a reamer for reaming an internal surface of each of the calcaneus and talus medullary canals, and targeting guide assembly for alignment with the subtalar joint. The lag screw member includes an elongated body, a first threaded portion at a first end and a bulbous portion at a second end. The targeting guide assembly receives a cutting blade in an elongated rod for reaming the articulating surfaces of the calcaneus and talus intramedullary canals, where the cutting blade is inserted through a percutaneous incision into the elongated rod.

24 Claims, 27 Drawing Sheets

U.S. PATENT DOCUMENTS

| | | | |
|---|---|---|---|
| 4,987,714 A | 1/1991 | Lemke | |
| 5,084,050 A | 1/1992 | Draenert | |
| 5,112,333 A | 5/1992 | Fixel | |
| 5,163,940 A | 11/1992 | Bourque | |
| 5,209,753 A | 5/1993 | Biedermann | |
| 5,350,380 A | 9/1994 | Goble et al. | |
| 5,403,321 A | 4/1995 | DiMarco | |
| 5,454,267 A | 10/1995 | Moreau et al. | |
| 5,456,267 A * | 10/1995 | Stark | 128/898 |
| 5,478,341 A | 12/1995 | Cook et al. | |
| 5,501,557 A | 3/1996 | Wakai | |
| 5,505,731 A | 4/1996 | Tornier | |
| 5,531,748 A | 7/1996 | de la Caffiniere | |
| 5,540,694 A | 7/1996 | DeCarlo, Jr. et al. | |
| 5,573,538 A | 11/1996 | Laboureau | |
| 5,601,550 A | 2/1997 | Esser | |
| 5,613,971 A | 3/1997 | Lower et al. | |
| 5,620,449 A | 4/1997 | Faccioli et al. | |
| 5,702,470 A | 12/1997 | Menon | |
| 5,718,705 A | 2/1998 | Sammarco | |
| 5,718,706 A | 2/1998 | Roger | |
| 5,741,266 A | 4/1998 | Moran | |
| 5,766,221 A | 6/1998 | Benderev et al. | |
| 5,779,704 A | 7/1998 | Kim | |
| 5,857,816 A | 1/1999 | Assmundson | |
| 5,865,559 A | 2/1999 | Yang | |
| 5,888,203 A | 3/1999 | Goldberg | |
| 5,891,150 A | 4/1999 | Chan | |
| 5,968,050 A | 10/1999 | Torrie | |
| 5,984,681 A | 11/1999 | Huang | |
| 5,997,541 A | 12/1999 | Schenk | |
| D420,132 S | 2/2000 | Bucholz et al. | |
| 6,019,761 A | 2/2000 | Gustilo | |
| 6,030,162 A | 2/2000 | Huebner | |
| 6,048,343 A | 4/2000 | Mathis et al. | |
| 6,106,528 A | 8/2000 | Durham et al. | |
| 6,120,511 A | 9/2000 | Chan | |
| 6,123,709 A | 9/2000 | Jones | |
| 6,123,711 A | 9/2000 | Winters | |
| 6,126,661 A | 10/2000 | Faccioli | |
| 6,168,595 B1 | 1/2001 | Durham et al. | |
| 6,168,597 B1 | 1/2001 | Biedermann et al. | |
| 6,174,119 B1 | 1/2001 | Orr | |
| 6,214,007 B1 | 4/2001 | Anderson | |
| 6,214,012 B1 | 4/2001 | Karpman et al. | |
| 6,221,074 B1 | 4/2001 | Cole et al. | |
| 6,235,031 B1 | 5/2001 | Hodgeman et al. | |
| 6,247,883 B1 | 6/2001 | Monserratt | |
| 6,254,605 B1 | 7/2001 | Howell | |
| 6,254,606 B1 | 7/2001 | Carney et al. | |
| 6,261,039 B1 | 7/2001 | Reed | |
| 6,261,290 B1 | 7/2001 | Friedl | |
| 6,270,499 B1 | 8/2001 | Leu et al. | |
| 6,280,442 B1 | 8/2001 | Barker et al. | |
| 6,287,313 B1 | 9/2001 | Sasso | |
| 6,379,362 B1 | 4/2002 | Birk et al. | |
| 6,402,753 B1 | 6/2002 | Cole et al. | |
| 6,402,757 B1 | 6/2002 | Moore et al. | |
| 6,423,064 B1 | 7/2002 | Kluger | |
| 6,435,788 B2 | 8/2002 | Reed | |
| 6,443,954 B1 | 9/2002 | Bramlet et al. | |
| 6,458,134 B1 | 10/2002 | Songer et al. | |
| 6,517,541 B1 | 2/2003 | Sesic | |
| 6,527,775 B1 | 3/2003 | Warburton | |
| 6,562,046 B2 | 5/2003 | Sasso | |
| 6,569,165 B2 | 5/2003 | Wahl et al. | |
| 6,589,245 B1 | 7/2003 | Weiler et al. | |
| 6,596,008 B1 | 7/2003 | Kambin | |
| 6,626,916 B1 | 9/2003 | Yeung et al. | |
| 6,629,976 B1 | 10/2003 | Gnos et al. | |
| 6,632,057 B1 | 10/2003 | Fauchet | |
| 6,634,844 B2 | 10/2003 | Huber | |
| 6,648,889 B2 | 11/2003 | Bramlet et al. | |
| 6,669,700 B1 | 12/2003 | Farris et al. | |
| 6,679,888 B2 | 1/2004 | Green et al. | |
| 6,685,706 B2 | 2/2004 | Padget et al. | |
| 6,692,496 B1 | 2/2004 | Wardlaw | |
| 6,692,503 B2 | 2/2004 | Foley et al. | |
| 6,695,844 B2 | 2/2004 | Bramlet et al. | |
| 6,709,436 B1 | 3/2004 | Hover et al. | |
| 6,712,849 B2 | 3/2004 | Re et al. | |
| 6,743,018 B1 | 6/2004 | Morrow | |
| 6,778,861 B1 | 8/2004 | Liebrecht et al. | |
| 6,793,659 B2 | 9/2004 | Putnam | |
| 6,808,527 B2 | 10/2004 | Lower et al. | |
| 6,849,093 B2 | 2/2005 | Michelson | |
| 6,875,216 B2 | 4/2005 | Wolf | |
| 6,908,271 B2 | 6/2005 | Breslin et al. | |
| 6,951,538 B2 | 10/2005 | Ritland | |
| 6,951,561 B2 | 10/2005 | Warren et al. | |
| 6,981,974 B2 | 1/2006 | Berger | |
| 7,018,380 B2 | 3/2006 | Cole | |
| 7,037,309 B2 | 5/2006 | Weil et al. | |
| 7,041,104 B1 | 5/2006 | Cole et al. | |
| 7,063,724 B2 | 6/2006 | Re et al. | |
| 7,074,221 B2 | 7/2006 | Michelson | |
| 7,144,399 B2 | 12/2006 | Hayes et al. | |
| 7,160,302 B2 | 1/2007 | Warburton | |
| 7,175,632 B2 | 2/2007 | Singhatat et al. | |
| 7,229,448 B2 | 6/2007 | Goble et al. | |
| 7,232,442 B2 | 6/2007 | Sohngen et al. | |
| 7,247,156 B2 | 7/2007 | Ekholm et al. | |
| 7,267,678 B2 | 9/2007 | Medoff | |
| 7,326,248 B2 | 2/2008 | Michelson | |
| 7,331,962 B2 | 2/2008 | Brånemark | |
| 7,341,588 B2 | 3/2008 | Swanson | |
| 7,344,538 B2 | 3/2008 | Myerson et al. | |
| 7,410,488 B2 | 8/2008 | Janna et al. | |
| 7,524,326 B2 | 4/2009 | Dierks | |
| 7,527,627 B2 | 5/2009 | Ferrante et al. | |
| 7,582,107 B2 | 9/2009 | Trail et al. | |
| 7,588,577 B2 | 9/2009 | Fencl et al. | |
| 7,591,819 B2 | 9/2009 | Zander | |
| 7,601,153 B2 | 10/2009 | Shinjo et al. | |
| 7,608,097 B2 | 10/2009 | Kyle | |
| 7,632,272 B2 | 12/2009 | Munro et al. | |
| 7,655,009 B2 | 2/2010 | Grusin | |
| 7,666,212 B2 | 2/2010 | Pathak | |
| 7,670,340 B2 | 3/2010 | Brivio et al. | |
| 7,713,271 B2 | 5/2010 | Warburton | |
| 7,717,947 B1 | 5/2010 | Wilberg et al. | |
| 7,731,721 B2 | 6/2010 | Rathbun et al. | |
| 7,731,738 B2 | 6/2010 | Jackson et al. | |
| 7,763,021 B2 | 7/2010 | Cole et al. | |
| 7,763,022 B2 | 7/2010 | Speitling et al. | |
| 7,763,023 B2 | 7/2010 | Gotfried | |
| 7,771,428 B2 | 8/2010 | Siravo et al. | |
| 7,785,326 B2 | 8/2010 | Green et al. | |
| 7,794,483 B2 | 9/2010 | Capanni | |
| 7,799,061 B2 | 9/2010 | Kay et al. | |
| 7,815,646 B2 | 10/2010 | Hart | |
| 7,842,036 B2 | 11/2010 | Phillips | |
| 7,867,231 B2 | 1/2011 | Cole | |
| 7,892,234 B2 | 2/2011 | Schlienger et al. | |
| 7,892,264 B2 | 2/2011 | Sanders et al. | |
| 7,909,825 B2 | 3/2011 | Saravia et al. | |
| 7,914,532 B2 | 3/2011 | Shaver et al. | |
| 7,918,853 B2 | 4/2011 | Watanabe et al. | |
| 7,922,748 B2 | 4/2011 | Hoffman | |
| 7,927,340 B2 | 4/2011 | Hart | |
| 7,938,848 B2 | 5/2011 | Sweeney | |
| 7,947,043 B2 | 5/2011 | Mutchler | |
| 8,034,056 B2 | 10/2011 | Fencl et al. | |
| 8,034,082 B2 * | 10/2011 | Lee et al. | 606/250 |
| 8,057,476 B2 | 11/2011 | Ekholm et al. | |
| 8,092,453 B2 | 1/2012 | Warburton | |
| 8,100,910 B2 | 1/2012 | Warburton | |
| 8,100,946 B2 * | 1/2012 | Strausbaugh et al. | 606/266 |
| 8,206,424 B2 | 6/2012 | Biedermann et al. | |
| 2001/0021852 A1 | 9/2001 | Chappius | |
| 2002/0052605 A1 | 5/2002 | Grooms et al. | |
| 2002/0128712 A1 | 9/2002 | Michelson | |
| 2002/0143333 A1 | 10/2002 | von Hoffmann et al. | |
| 2002/0169453 A1 | 11/2002 | Berger | |
| 2002/0197134 A1 | 12/2002 | Huber | |
| 2003/0028193 A1 | 2/2003 | Weil et al. | |
| 2003/0060827 A1 | 3/2003 | Coughlin | |

| | | | |
|---|---|---|---|
| 2003/0065391 A1 | 4/2003 | Re et al. |
| 2003/0083667 A1 | 5/2003 | Ralph et al. |
| 2003/0147716 A1 | 8/2003 | Nagawa |
| 2003/0158555 A1 | 8/2003 | Sanders |
| 2003/0229346 A1 | 12/2003 | Oribe et al. |
| 2004/0006345 A1 | 1/2004 | Vlahos et al. |
| 2004/0082959 A1 | 4/2004 | Hayes |
| 2004/0097945 A1 | 5/2004 | Wolf |
| 2004/0172031 A1 | 9/2004 | Rubecamp et al. |
| 2004/0181234 A1 | 9/2004 | McDevitt et al. |
| 2004/0220570 A1 | 11/2004 | Frigg |
| 2005/0015092 A1 | 1/2005 | Rathbun et al. |
| 2005/0069397 A1 | 3/2005 | Shavit et al. |
| 2005/0107791 A1 | 5/2005 | Manderson |
| 2005/0125070 A1 | 6/2005 | Reiley |
| 2005/0149030 A1 | 7/2005 | Serhan et al. |
| 2005/0171544 A1 | 8/2005 | Falkner, Jr. |
| 2005/0171546 A1 | 8/2005 | Wolf |
| 2005/0192580 A1 | 9/2005 | Dalton |
| 2005/0251147 A1 | 11/2005 | Novak |
| 2005/0273101 A1 | 12/2005 | Schumacher |
| 2005/0277940 A1 | 12/2005 | Neff |
| 2005/0283159 A1 | 12/2005 | Amara |
| 2006/0009774 A1 | 1/2006 | Goble et al. |
| 2006/0009846 A1 | 1/2006 | Trieu et al. |
| 2006/0015101 A1 | 1/2006 | Warburton et al. |
| 2006/0052787 A1 | 3/2006 | Re et al. |
| 2006/0095039 A1 | 5/2006 | Mutchler |
| 2006/0122600 A1 | 6/2006 | Cole |
| 2006/0122612 A1 | 6/2006 | Justin et al. |
| 2006/0142770 A1 | 6/2006 | Capanni |
| 2006/0149244 A1* | 7/2006 | Amrein et al. ............. 606/61 |
| 2006/0173461 A1 | 8/2006 | Kay et al. |
| 2006/0189991 A1 | 8/2006 | Bickley |
| 2006/0200143 A1 | 9/2006 | Warburton |
| 2006/0200144 A1 | 9/2006 | Warburton |
| 2006/0200160 A1 | 9/2006 | Border et al. |
| 2006/0206044 A1 | 9/2006 | Simon |
| 2006/0235396 A1 | 10/2006 | Sanders et al. |
| 2006/0241608 A1 | 10/2006 | Myerson et al. |
| 2006/0241777 A1 | 10/2006 | Partin et al. |
| 2006/0264954 A1 | 11/2006 | Sweeney, II et al. |
| 2007/0021839 A1 | 1/2007 | Lowe |
| 2007/0038306 A1 | 2/2007 | O'Gara |
| 2007/0055286 A1 | 3/2007 | Ralph et al. |
| 2007/0066977 A1 | 3/2007 | Assell et al. |
| 2007/0073290 A1 | 3/2007 | Boehm, Jr. |
| 2007/0093841 A1 | 4/2007 | Hoogland |
| 2007/0112432 A1* | 5/2007 | Reiley ............. 623/21.18 |
| 2007/0173835 A1 | 7/2007 | Medoff |
| 2007/0233114 A1 | 10/2007 | Bouman |
| 2007/0270848 A1 | 11/2007 | Lin |
| 2007/0270855 A1 | 11/2007 | Partin |
| 2008/0065224 A1 | 3/2008 | Reigstad et al. |
| 2008/0091203 A1 | 4/2008 | Warburton et al. |
| 2008/0154271 A1 | 6/2008 | Berberich et al. |
| 2008/0208261 A1 | 8/2008 | Medoff |
| 2008/0221623 A1 | 9/2008 | Gooch |
| 2008/0269908 A1 | 10/2008 | Warburton |
| 2008/0279654 A1 | 11/2008 | Deschamps |
| 2008/0294164 A1 | 11/2008 | Frank et al. |
| 2008/0306487 A1 | 12/2008 | Hart |
| 2008/0306537 A1 | 12/2008 | Culbert |
| 2009/0018542 A1 | 1/2009 | Saravia et al. |
| 2009/0048600 A1 | 2/2009 | Matityahu et al. |
| 2009/0062797 A1 | 3/2009 | Huebner |
| 2009/0088767 A1 | 4/2009 | Leyden et al. |
| 2009/0088804 A1 | 4/2009 | Kyle et al. |
| 2009/0088806 A1 | 4/2009 | Leyden et al. |
| 2009/0093813 A1 | 4/2009 | Elghazaly |
| 2009/0093849 A1 | 4/2009 | Grabowski |
| 2009/0093851 A1 | 4/2009 | Osman |
| 2009/0099571 A1* | 4/2009 | Cresina et al. ............. 606/96 |
| 2009/0149857 A1* | 6/2009 | Culbert et al. ............. 606/80 |
| 2009/0157077 A1 | 6/2009 | Larsen et al. |
| 2009/0157078 A1 | 6/2009 | Mikol |
| 2009/0157079 A1 | 6/2009 | Warburton et al. |
| 2009/0157080 A1 | 6/2009 | Warburton |
| 2009/0177203 A1 | 7/2009 | Reiley |
| 2009/0198289 A1 | 8/2009 | Manderson |
| 2009/0209961 A1 | 8/2009 | Ferrante et al. |
| 2009/0240252 A1* | 9/2009 | Chang ............. 606/96 |
| 2009/0248025 A1 | 10/2009 | Haidukewych et al. |
| 2009/0264885 A1 | 10/2009 | Grant et al. |
| 2009/0281580 A1 | 11/2009 | Emannuel |
| 2009/0292292 A1 | 11/2009 | Fencl et al. |
| 2009/0306666 A1 | 12/2009 | Czartoski et al. |
| 2010/0023011 A1 | 1/2010 | Nakamura |
| 2010/0023064 A1 | 1/2010 | Brunger et al. |
| 2010/0030280 A1 | 2/2010 | Jackson |
| 2010/0042164 A1 | 2/2010 | Lee et al. |
| 2010/0042167 A1 | 2/2010 | Nebosky et al. |
| 2010/0057141 A1 | 3/2010 | Abdelgany et al. |
| 2010/0069970 A1 | 3/2010 | Lewis et al. |
| 2010/0076499 A1 | 3/2010 | McNamara et al. |
| 2010/0121325 A1 | 5/2010 | Tyber et al. |
| 2010/0179551 A1 | 7/2010 | Keller et al. |
| 2010/0256638 A1 | 10/2010 | Tyber et al. |
| 2010/0256639 A1 | 10/2010 | Tyber et al. |
| 2010/0312279 A1 | 12/2010 | Gephart et al. |
| 2010/0324556 A1 | 12/2010 | Tyber et al. |
| 2011/0004255 A1 | 1/2011 | Weiner et al. |
| 2011/0022066 A1 | 1/2011 | Sevrain |
| 2011/0046681 A1 | 2/2011 | Prandi et al. |
| 2011/0060337 A1 | 3/2011 | Ferrante et al. |
| 2011/0118739 A1 | 5/2011 | Tyber et al. |
| 2011/0125153 A1 | 5/2011 | Tyber et al. |
| 2011/0144645 A1 | 6/2011 | Saravia et al. |
| 2011/0218580 A1 | 9/2011 | Schwager et al. |
| 2011/0282398 A1 | 11/2011 | Overes et al. |
| 2011/0301651 A1 | 12/2011 | Kirschman |
| 2012/0004690 A1 | 1/2012 | Gonzalez-Hernandez |
| 2012/0010669 A1 | 1/2012 | O'Neil et al. |
| 2012/0016424 A1 | 1/2012 | Kave |
| 2012/0022603 A1 | 1/2012 | Kirschman |
| 2012/0095516 A1 | 4/2012 | Dikeman |
| 2012/0109213 A1 | 5/2012 | Appenzeller et al. |

FOREIGN PATENT DOCUMENTS

WO    WO 2007131287    11/2007

\* cited by examiner

INTRAMEDULLARY FIXATION SCREW, A FIXATION SYSTEM, AND METHOD OF FIXATION OF THE SUBTALAR JOINT

CROSS-REFERENCE TO RELATED APPLICATIONS

This application is a continuation-in-part application of Non-Provisional application Ser. No. 12/658,680, filed Feb. 11, 2010, which is a continuation-in-part application of Non-Provisional application Ser. No. 12/456,808, filed Jun. 23, 2009, which claims the benefit of Provisional Application No. 61/132,932, filed Jun. 24, 2008, the entire contents of the entire chain of applications are herein incorporated by reference.

FIELD OF THE INVENTION

This invention relates to the field of orthopedic implant devices, and more particularly, to an intramedullary screw used for fusion of the angled joints, bones and deformity correction, such as the subtalar joint in the foot.

BACKGROUND OF THE INVENTION

Orthopedic implant devices, such as intramedullary nails, plates, rods and screws are often used to repair or reconstruct bones and joints affected by trauma, degeneration, deformity and disease, such as Charcot arthropathy caused by diabetes in some patients, Hallux Valgus deformities, failed Keller Bunionectomies, Rheumatoid Arthritis, and severe deformities.

Moreover, infections and wound complications are a major concern in the aforementioned procedures. Wound closure is technically demanding for the surgeon, and devices that add surface prominence, such as plates or exposed screws, add to this difficulty by requiring greater tissue tension during incision reapproximation. This increases the risk of postoperative wound infections and dehiscence that may ultimately result in limb amputation.

Various implants have been utilized for surgical treatment of these bones and joints, including bone screws. Implants have also been utilized to treat severe deformities in the metatarsal and phalangeal bones, including multiple screws and plates. These multiple screws and plates have been commonly used in a first metatarsal-phalangeal fusion procedure to fuse the first metatarsal to the first phalangeal bone in hallux valgus deformities, failed keller bunionectomies, rheumatoid arthritis, and other types of severe deformities in the metatarsal and phalange bones. While these devices allow fixation and promote fusion, they do not deliver restoration of the arch in a Charcot foot, they are not effective in metatarsal-phalangeal (MTP) fusion procedures, nor do they deliver uniform compression for various predetermined angles of compression.

Particularly, screw implants in MTP procedures are ineffective in delivering sufficient compression to the bones in the foot, preventing screw head break out, or delivering effective bending resistance. Moreover, hard to control dorsiflexion and valgus angles as well skin irritation from proximity to the skin prevents these screw implants from being readily utilized for surgical treatment. Yet further, plate implants used with bone screws too have the same drawbacks as fixed varus and valgus angles, lack of direct compression across the MTP joint, and skin irritations from proximity to the skin reduce the effectiveness of these implants.

There is therefore a need for an intramedullary fixation screw and method of use that overcomes some or all of the previously delineated drawbacks of prior fixation assemblies.

SUMMARY OF THE INVENTION

An object of the invention is to overcome the drawbacks of previous inventions.

Another object of the invention is to provide a novel and useful intramedullary fixation screw that may be utilized to treat bones in a human body.

Another object of the invention is to provide a system and method for compressing bones using an intramedullary fixation screw.

Another object of the invention is to align the subtalar joint through the use of an intramedullary screw.

Another object of the invention is to provide a system for aligning the talocalcaneal joint in a human foot.

In a first non-limiting aspect of the invention, an intramedullary fixation system for fixation of the subtalar joint is provided and includes a lag screw member, a reamer, and a targeting guide assembly. The lag screw member includes an elongated body, a threaded portion at a first end and a bulbous portion at a second end. The reamer is provided for reaming an internal surface of each of the calcaneus and talus medullary canals. Also, the targeting guide assembly is provided for aligning a cutting blade with the subtalar joint.

In a second non-limiting aspect of the invention, a method for fusion of the subtalar joint includes several steps. In one step, a lag screw member is provided. In another step, a hole is drilled in each of the calcaneus and talus medullary canals. In another step, an internal surface of the calcaneus and talus medullary canals is reamed. In another step, a targeting guide assembly is provided consisting of an elongated rod, a circular handle and a alignment guide. In another step, the elongated rod is inserted into the drilled hole at a predetermined depth. In another step, the alignment guide is aligned with the subtalar joint. In another step, a cutting blade is inserted into a percutaneous incision and into the elongated rod. In another step, a plurality of articulating surfaces of the calcaneus and talus medullary canals is reamed. In another step, the lag screw member is inserted into the drilled hole. Finally, compression may be applied to the lag screw member causing the subtalar joint to be compressed

BRIEF DESCRIPTION OF THE DRAWINGS

A further understanding of the invention can be obtained by reference to a preferred embodiment set forth in the illustrations of the accompanying drawings. Although the illustrated embodiment is merely exemplary of systems and methods for carrying out the invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the invention, reference is now made to the following drawings in which.

DETAILED DESCRIPTION OF THE INVENTION

The invention may be understood more readily by reference to the following detailed description of preferred embodiment of the invention. However, techniques, systems, and operating structures in accordance with the invention may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein, which define the scope of the invention. It must be noted that, as used in the specification and the appended claims, the singular forms "a", "an", and "the" include plural referents unless the context clearly indicates otherwise.

Figure 1:
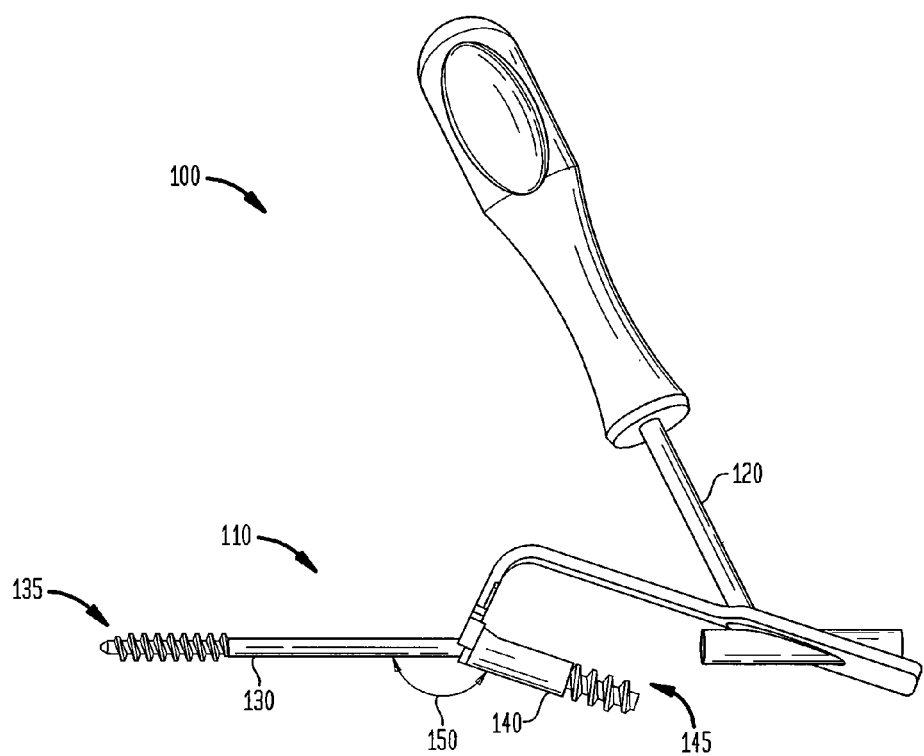
FIG. 1 is a perspective view of a fixation system according to a preferred embodiment of the invention.

Referring now to FIG. 1, there is shown a fixation system 100 which is made in accordance with the teachings of the preferred embodiment of the invention. As shown, the fixation system 100 includes an intramedullary fixation assembly 110, comprising a proximal screw member 130 and a distal member 140. Proximal screw member 130 is provided on proximal end 135 of assembly 110 and is coupled to a distal member 140 that is provided on the distal end 145 of the fixation assembly 110. Also, proximal screw member 130 makes a fixed angle 150 with distal member 140 and this angle 150 determines the angle for arch restoration. Moreover, fixation system 100 includes instrument 120 that is utilized to couple intramedullary fixation assembly 110 to the bones in the mid-foot region (not shown). It should be appreciated that in one non-limiting embodiment, intramedullary fixation assembly 110 may be made from a Titanium material, although, in other non-limiting embodiments, intramedullary fixation assembly 110 may be made from SST, PEEK, NiTi, Cobalt chrome or other similar types of materials.

Figure 2:
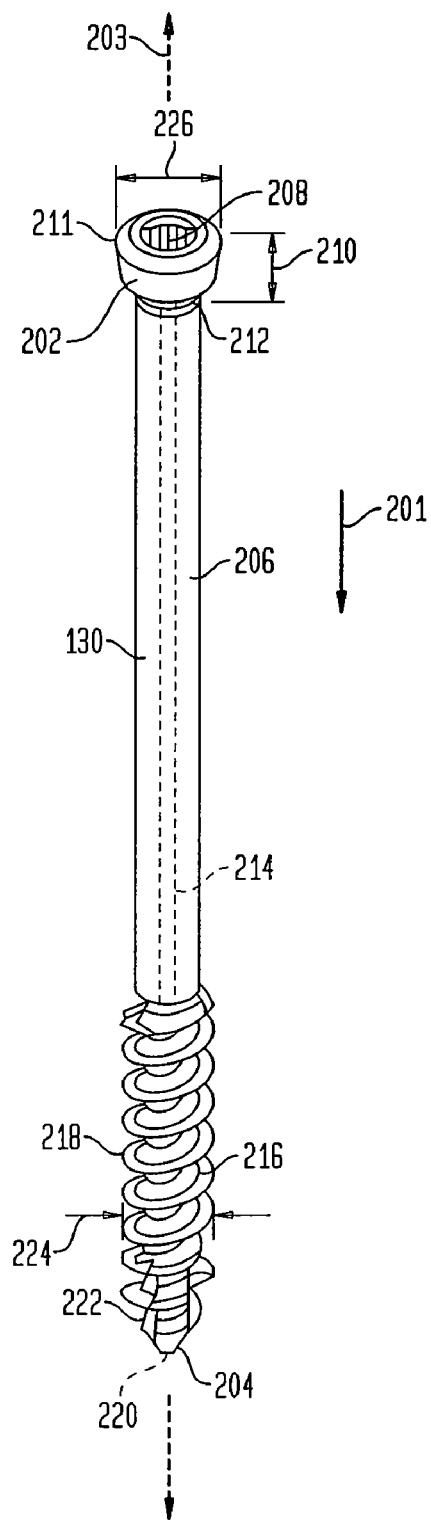
FIG. 2 is a perspective view of a proximal screw member used in the fixation system shown in FIG. 1 according to the preferred embodiment of the invention.

As shown in FIG. 2, proximal screw member 130 is generally cylindrical in shape and extends from first bulbous portion 202 (or annular portion) to second tapered end 204. End 204 has a diameter that is slightly smaller than diameter 226 of bulbous portion 202. Additionally, bulbous portion 202 has a taper, such as a Morse taper, with a width that decreases from end 211 to end 212. The taper allows for a locked interference fit with tapered aperture 316 (such as that which is achieved by friction after the parts are pushed together) when tapered bulbous portion 202 is combined with tapered aperture 316, shown and described below. Moreover, bulbous portion 202 is generally circular and has a generally hexagonal torque-transmitting aperture 208 that traverses length 210 of bulbous portion 202. However, a star-shaped aperture, a square-shaped aperture, or any other shaped aperture may be utilized without departing from the scope of the invention. Torque transmitting aperture 208 is utilized to transmit a torque from bulbous portion 202 to tapered end 204 by rotating bulbous portion 202.

Further, proximal screw member 130 has a first smooth exterior portion 206 extending from end 212 of bulbous portion 202. Portion 206 comprises an internal aperture 214 that longitudinally traverses portion 206 in direction 201. Portion 206 terminates into a second generally tubular portion 216. Portion 216 may comprise internal circular aperture 220 that longitudinally traverses inside portion 216. Internal circular aperture 220 is aligned with apertures 214 and 208 along axis 203 to form a continuous opening (i.e., a cannula) from bulbous portion 202 to end 204. The continuous opening or cannula is provided to interact with a guide wire (not shown) by receiving the guide wire within the continuous opening thereby positioning and locating the proximal member 130. In other non-limiting embodiments, the proximal member 130 may be provided without apertures 220 and 214 (i.e., the proximal member is solid).

Furthermore, tubular portion 216 has a plurality of circular threads, such as threads 218, which are circumferentially (i.e., spirally) disposed on the external surface of portion 216 and, with threads 218 having an external diameter 224. Portion 216 may also be provided with a self-tapping leading edge 222 to provide portion 216 with the ability to remove bone material during insertion of proximal screw member 130 into bone. It should be appreciated that the length of the proximal member 130 may be selected of varying lengths to allow a surgeon to fuse different joints in a foot (not shown).

Figure 3A:
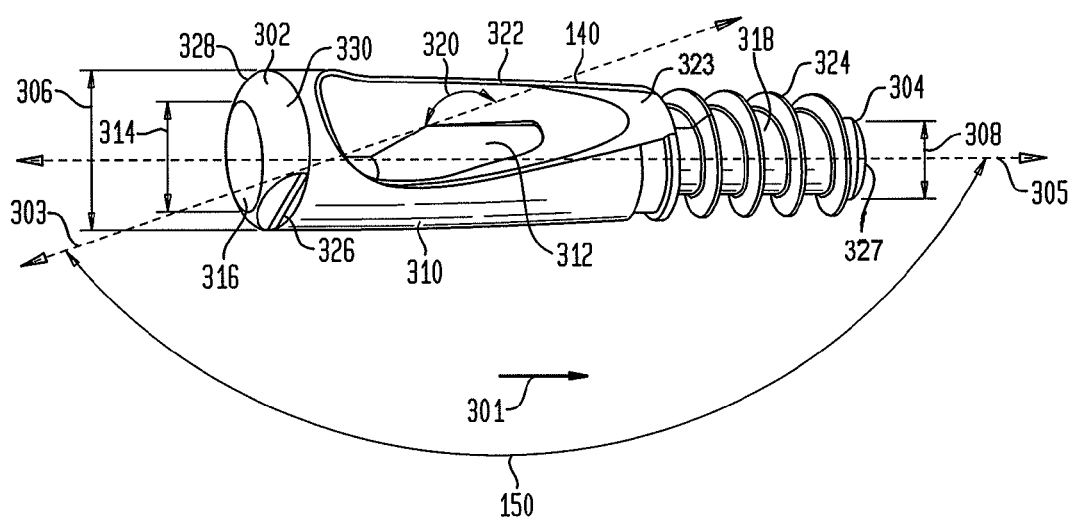
FIG. 3A is a perspective view of a distal member used in the fixation system shown in FIG. 1 according to the preferred embodiment of the invention.
Figure 3B:
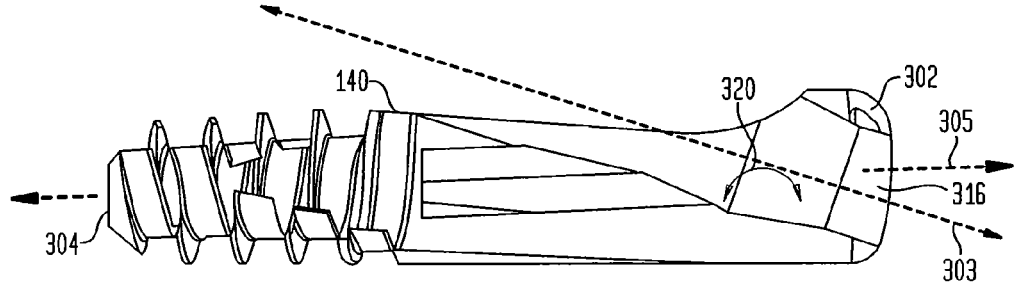
FIG. 3B is a perspective cross-sectional view of the distal member shown in FIG. 3A according to the preferred embodiment of the invention.

As shown in FIGS. 3A-3B, distal member 140 of the preferred embodiment is generally tubular in shape and tapers from a first end 302 to a second end 304 (i.e. end 302 has a diameter 306 that is slightly larger than diameter 308 of end 304). However, in another non-limiting embodiment, distal member 140 has a constant width from first end 302 to second end 304. Further, first end 302 is generally semi-spherical in shape and has an internal circular aperture 316, which traverses end 302 along direction 301 (i.e. end 302 is generally "donut" shaped). Additionally, circular aperture 316 emanates from surface 322, such that portion 310 has a generally tapered aperture 316 provided in portion 310. Circular aperture 316 comprises slope 320 from first end 302 to end 323 of portion 310. Further, aperture 316 is aligned along axis 303, which is offset from horizontal axis 305 of distal member 140. Axis 303 forms an angle 150 with horizontal axis 305 that determines the angle for arch restoration, as shown in FIG. 3A. Angle 150 may be any angle greater than 90 degrees and less than 180 degrees. Tapered aperture 316 when combined with tapered bulbous portion 202, shown in FIG. 2, creates a locked interference fit between proximal member 130 and distal member 140. First end 302 has a plurality of substantially similar grooves 326 and 328, which form an "L-shape" with surface 330 of end 302. Grooves 326 and 328 are provided to receive instrument 120 of fixation system 100, which is later described. In other non-limiting embodiments, other similar instruments may be provided to be received within grooves 326 and 328.

Distal member 140 further comprises a generally smooth portion 310 coupled to end 302. Portion 310 has a generally hexagonal shaped aperture 312, which opens into aperture 316 and which longitudinally traverses through portion 310 in direction 301. In other non-limiting embodiments, a star-shaped aperture, a square-shaped aperture, or any other shaped aperture may be utilized. Circular aperture 316 has a diameter 314 that is slightly larger than external diameter 224 of portion 216 and 206 of proximal screw member 130, with portions 216 and 206 being slidably received within aperture 316 of portion 310. Aperture 316 has a diameter that is smaller than diameter 226 of bulbous portion 202.

Portion 310 of distal member 140 terminates into a second generally cylindrical portion 318 which has a plurality of threads 324, which are circumferentially disposed on the external surface of portion 318. Portion 318 has an internal circular aperture 327 which is longitudinally coextensive with portion 318 in direction 301. Circular aperture 327 aligns with aperture 312 to form a continuous opening from end 302 to end 304.

Figure 4:
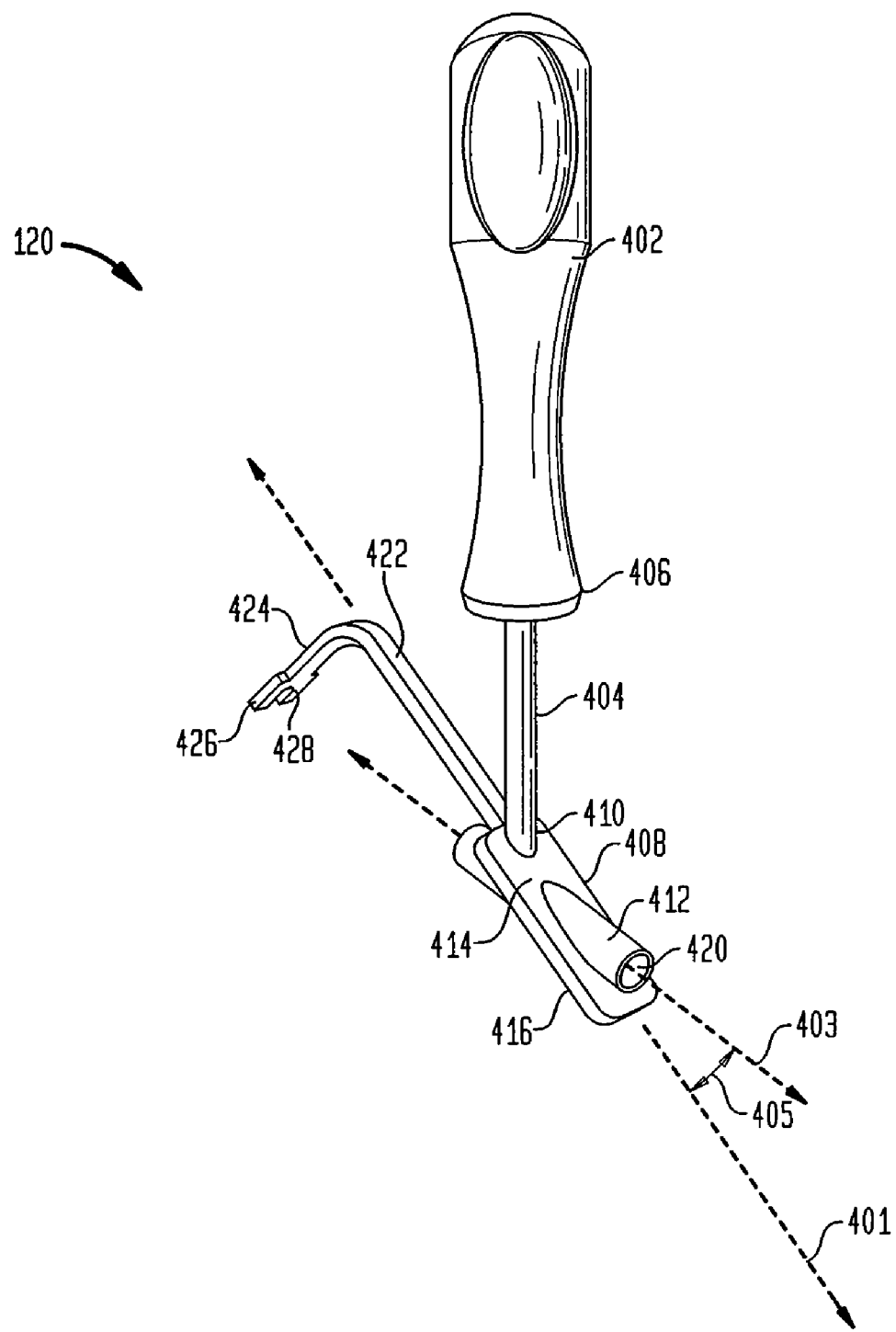
FIG. 4 is a perspective view of the instrument member used in the fixation system shown in FIG. 1 according to the preferred embodiment of the invention.

As shown in FIG. 4, instrument 120 is illustrated for coupling proximal screw member 130 to distal member 140. Particularly, instrument 120 includes a handle portion 402 coupled to a rod portion 404. Rod portion 404 emanates from handle portion 402 at end 406 and terminates into a rectangular planar portion 408 at end 410. Planar portion 408 is aligned along axis 401 and is fixably coupled to a generally cylindrical tubular portion 412 (i.e., an aiming device). Portion 412 traverses portion 408 from top surface 414 to bottom surface 416. Further, tubular portion 412 is aligned along dissimilar axis 403, forming an angle 405 with axis 401. Also, tubular portion 412 has a through aperture 420 that longitudinally traverses portion 412 along axis 403.

Planar portion 408 is coupled to planar portion 422, with portion 422 having a width slightly smaller than width of portion 408. Portion 422 terminates into a generally "U-shaped" portion 424 with portion 424 being orthogonal to portion 422. Further, portion 424 has a plurality of substantially similar sides 426 and 428 which are provided to be slidably coupled to grooves 326 and 328 of distal member 140.

In operation, sides 426 and 428 of instrument 120 are received in respective grooves 326 and 328 of distal member 140, of FIGS. 3A-3B, thereby slidably coupling distal member 140 to instrument 120. In this position, axis 303 of aperture 316 is aligned along substantially the same axis as axis 403 of instrument 120. Proximal screw member 130 is coupled to distal member 140 by slidably coupling portions 206 and 216 through aperture 420 of tubular portion 412. Tubular portion 412 guides proximal screw member 130 through internal aperture 420 and into aperture 316 on surface 322 and may also guide a Kirschner wire (K wire) or a drill. Proximal screw member 130, of FIG. 2, travels into bone as portions 216 and 206 travel further through aperture 316 at end 302 until bulbous portion 202 is restrained by surface 322 and end 302. Aperture 316, being tapered along axis 303, causes proximal screw member 130 to form an angle 150 with distal member 140, with proximal member 130 being aligned along an axis 303, which is substantially the same axis as axis 403 of tubular portion 412 of instrument 120.

Figure 5:
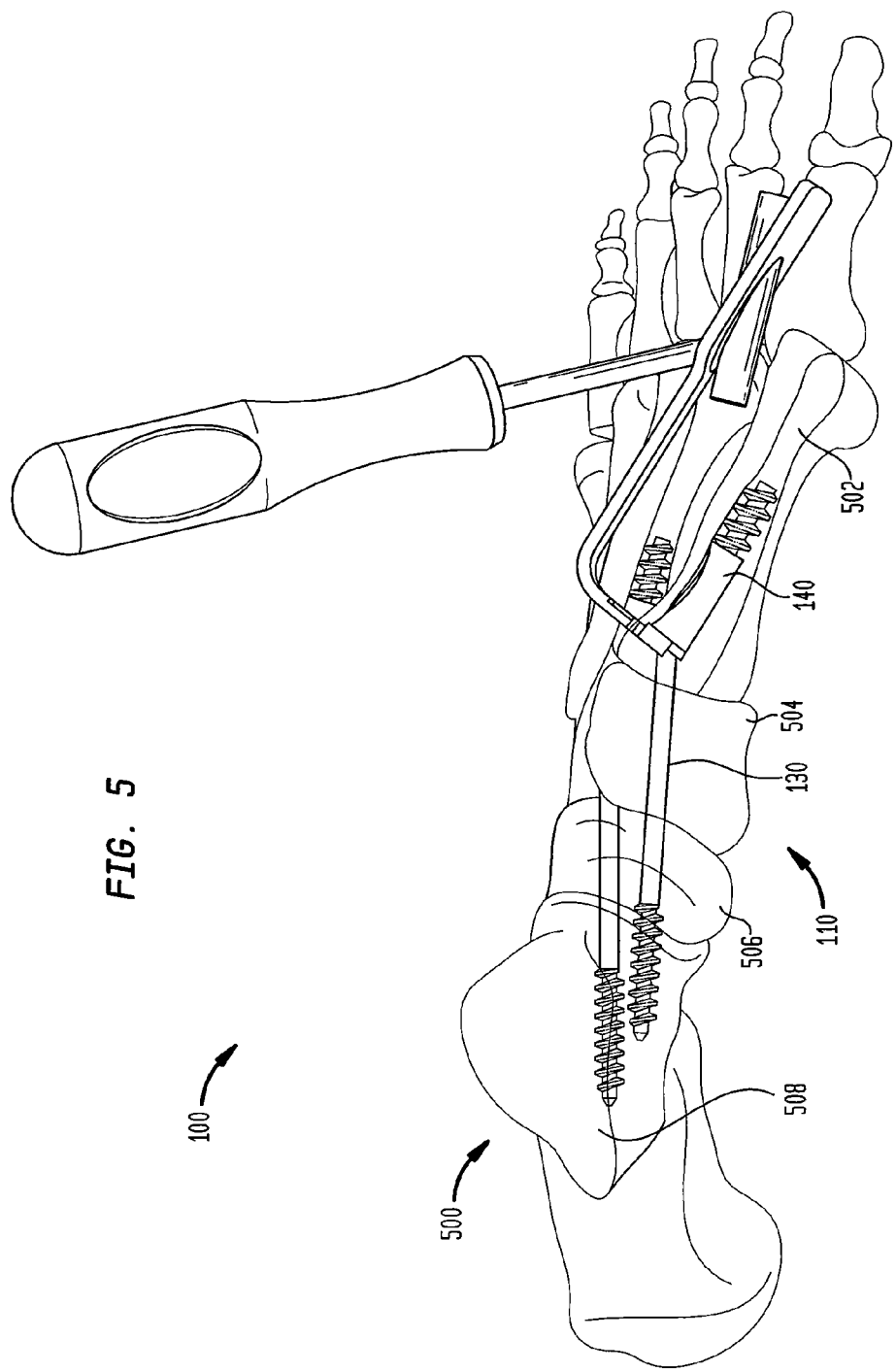
FIG. 5 is a perspective view of the assembled intramedullary fixation assembly inserted into the bones of a patient's foot according to the preferred embodiment of the invention.
Figure 6:
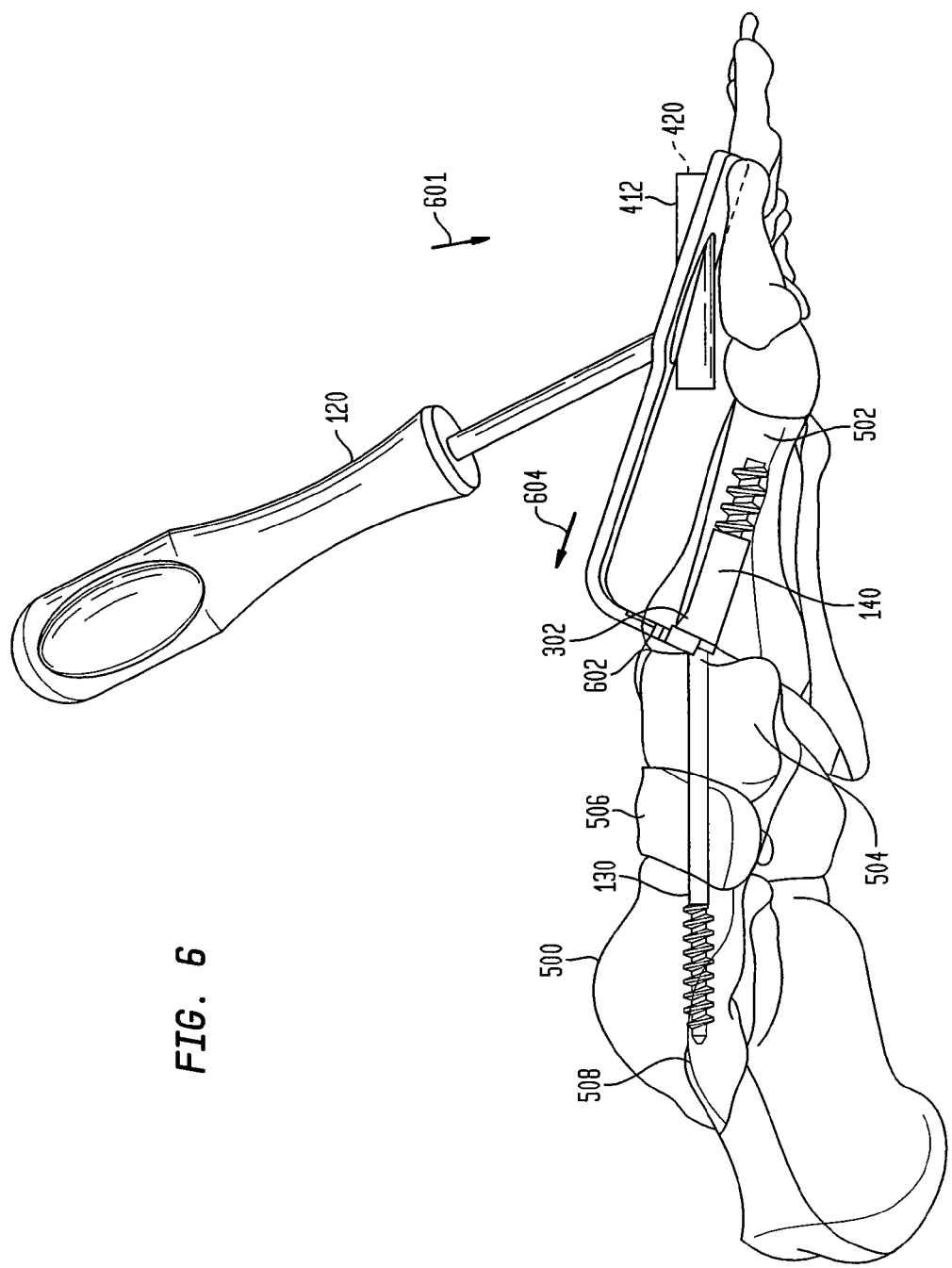
FIG. 6 is a side view of the assembled intramedullary fixation assembly shown in FIG. 5 according to the preferred embodiment of the invention.
Figure 7:
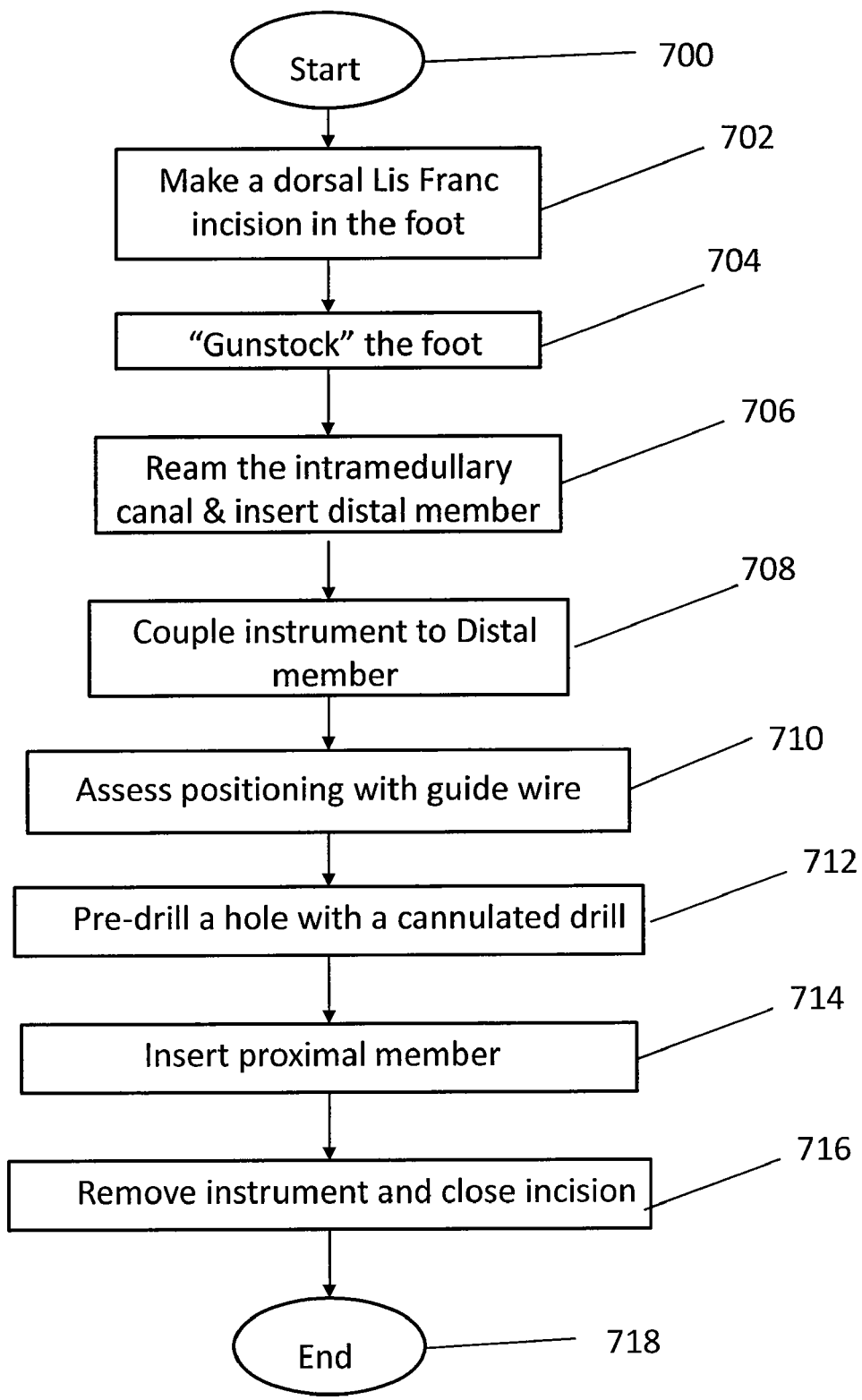
FIG. 7 is a flow chart illustrating the method of coupling the intramedullary fixation assembly shown in FIGS. 1-6 to tarsal and metatarsal bones in a patient's foot according to the preferred embodiment of the invention.

In operation, and as best shown in FIGS. 5, 6 and 7, the fixation system 100 utilizes the intramedullary fixation assembly 110 for treating and fixating the deteriorated and damaged or fractured bones in the human foot 500. This restores the arch in a human foot 500 by coupling the intramedullary fixation assembly 110 to the human foot 500 of a left leg. In one-non limiting example, and as shown in FIG. 5, the intramedullary assembly 110 is coupled to the medullary canals of the first metatarsal 502, medial cuneiform 504, navicular 506 and talus bone 508. Talus bone 508 makes up part of the ankle joint where the threaded portion 216 of the proximal screw member 130 of the intramedullary assembly 110 is threadably coupled. The medial cuneiform 504 and navicular 506 bones are most affected by Diabetic Charcot foot disorder that causes deterioration and collapse of the arch of the foot 500. It should be appreciated that the intramedullary assembly 110 may be used within each of the five rays, with a ray representing a line drawn from each metatarsal bone to the talus. The angulation in the smaller rays will be smaller than the two rays (i.e., a line from the first and second metatarsal bones to the talus bone). Also, the diameter of distal member 140 will decrease from the large ray to the small ray. In one non-limiting example, the angulation may be any angle greater than 90 degrees and less than 180 degrees. For example, the angle for the first ray may be 150-170 degrees and the angles for the other rays may be 160-175 degrees.

As shown in FIGS. 6 and 7, the intramedullary fixation assembly 110 may be utilized to reconstruct an arch in a mid-foot region of a human foot 500. As shown, the method starts in step 700 and proceeds to step 702, whereby a Dorsal Lis Franc incision (i.e., mid-foot incision) (not shown) is made in foot 500 in order to gain access to the joint. In step 704, the joint capsule is separated by "Gunstocking" foot 500 in direction 601 (i.e., the foot 500 is bent mid-foot) to expose the articular surface 602 and the articulating cartilage is removed. Next, in step 706, the intramedullary canal is reamed and the distal member 140 is inserted into the intramedullary canal (not shown) of the metatarsal 502. In other non-limiting embodiments, the distal member 140 may be inserted by impaction, by press fit, by reaming a hole in the intramedullary canal (not shown) or substantially any other similar strategy or technique.

Next, in step 708, the instrument 120 is coupled to the distal member 140 by coupling sides 426 and 428 of instrument 120 to respective grooves 326 and 328. In step 710, initial positioning of the proximal member 130 is assessed with the use of a guide wire through portion 412 (i.e., aiming device). Next, in step 712, a countersink drill is inserted through portion 412 and the proximal cortex is penetrated. In this step, a cannulated drill or guide wire is used to pre-drill the hole through the joints selected for fusion. In step 714, the proximal screw member 130 is inserted over the guide wire and into the distal member 140. Particularly, the proximal member 130 is inserted through tubular portion 412 (i.e., aiming device), causing proximal member 130 to travel through internal longitudinal aperture 420, into distal member 140 and further into bones 504, 506 and 508 until rigid connection with the tapered aperture 316 is made, thereby compressing the joint. In one non-limiting embodiment, a locking element (not shown) such as a plate or a washer is coupled to end 302 of the intramedullary fixation assembly 110 to further secure proximal threaded member 130 to distal member 140. Next, in step 716 the instrument 120 is removed and the dorsal Lis Franc (i.e., mid-foot) incision is closed. The method ends in step 718.

It should be appreciated that a plurality of intramedullary fixation assemblies, such as intramedullary fixation assembly 110, may be inserted into any of the bones of a foot 500 such as, but not limited to the metatarsal, cuneiform, calcaneus, cuboids, talus and navicular bones, in order to restore the natural anatomical shape of the arch of the foot 500. Thus, the fixation system 100, in one non-limiting embodiment, is utilized to couple the intramedullary fixation assembly 110 to the foot 500, which causes the metatarsal 504, medial cuneiform 504, navicular 506 and talus 508 bones to be aligned to the proper anatomical shape of an arch when assembled within foot 500. It should be appreciated that the intramedullary fixation assembly 110 is delivered through a dorsal midfoot incision, thereby reducing the disruption to the plantar tissues and/or the metatarsal heads while at the same time minimizing the tension on the skin. This allows for improved wound closure, reduced operating room time, reduction in the number of incisions required and reduction in the total length of incisions. It should also be appreciated that in other non-limiting embodiments, the intramedullary assembly 110 may be utilized with graft material (i.e., autograft, allograft or other biologic agent).

Figure 8:
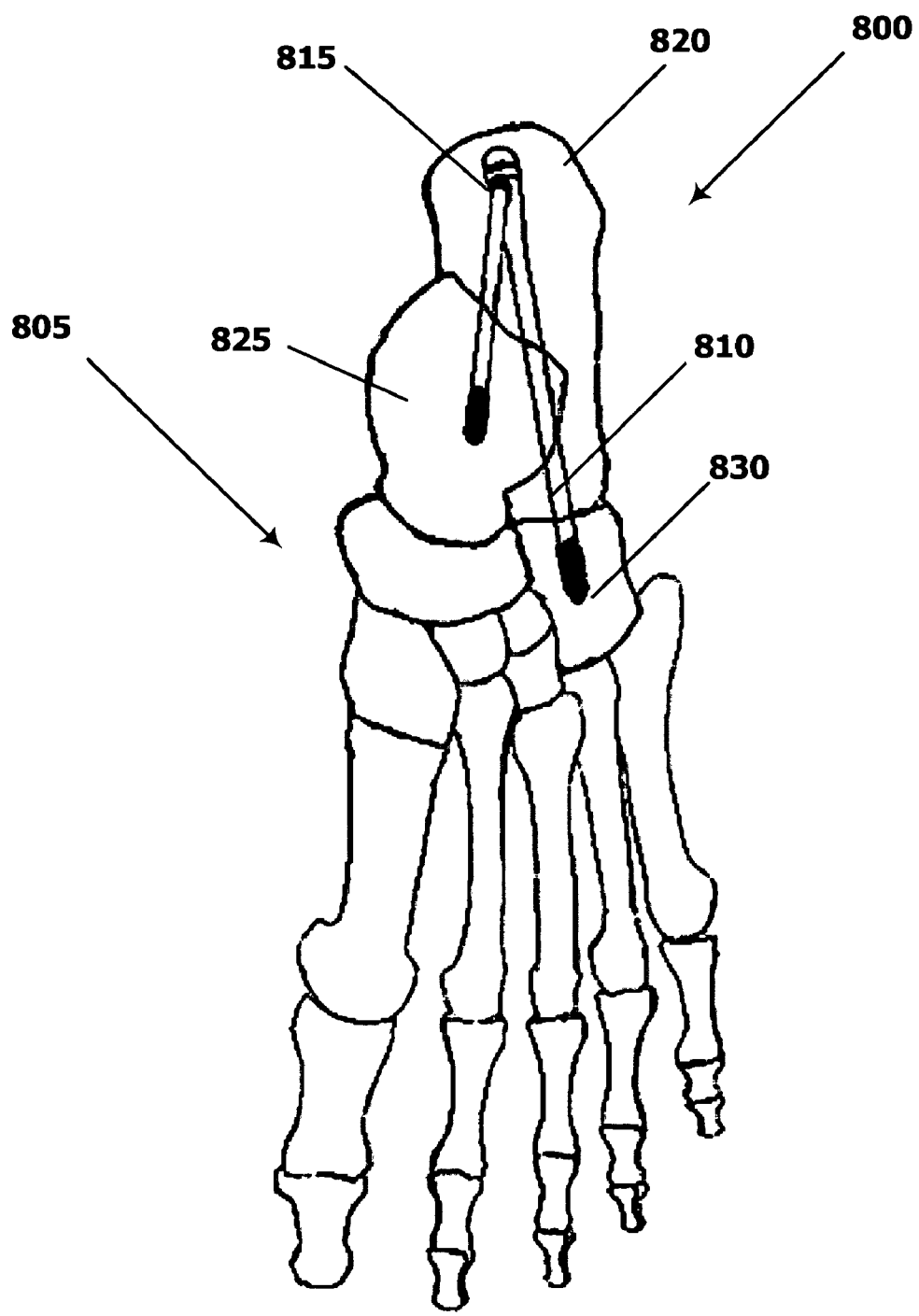
FIG. 8 is a perspective view of an assembled intramedullary fixation assembly inserted into the bones of a patient's foot according to an alternate embodiment of the invention.

In an alternate embodiment, as shown in FIG. 8, an intramedullary fixation assembly 800 is provided in order to apply intraosseous compression to bones. Particularly, the intramedullary fixation assembly 800 comprises a tapered screw member 810 coupled to a lag screw member 815 at a fixed acute angle for the internal fusion of the bones of the human foot 805, such as, for example, the calcaneus bone 820, the talus bone 825, and the cuboids bone 830. In other non-limiting embodiments, the intramedullary fixation assembly 800 may be utilized for any other appropriate use for the internal fixation of the other bones. It should be appreciated that the intramedullary fixation assembly 800 may be provided at several lengths for the internal fixation of a variety of bone sizes in the human body.

Figure 9:
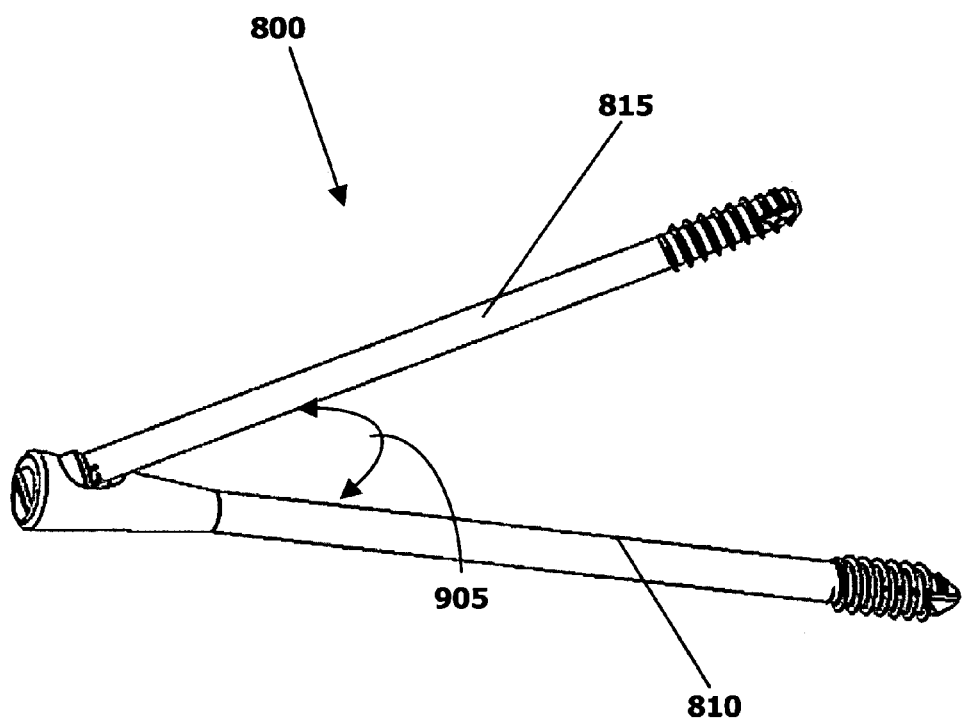
FIG. 9 is a perspective view of the intramedullary fixation assembly shown in FIG. 8 according to the alternate embodiment of the invention.

Also as shown in FIG. 9, the intramedullary fixation assembly 800 includes the tapered screw member 810 coupled to the lag screw member 815 at a fixed angle 905. The fixed angle 905 may be provided at various fixed angles depending on the bone segments that are being compressed. The fixed angle between the tapered screw member 810 and the lag screw member 815 causes the intramedullary fixation assembly 800 to "hook" into the bone segments and translates the compression applied to bone fragments across the members 810 and 815. It should be appreciated that in one non-limiting embodiment, the intramedullary fixation assembly 800 may be made from a Titanium material, although, in other non-limiting embodiments, the intramedullary fixation assembly 800 may be made from SST, PEEK, NiTi, Cobalt chrome or other similar types of materials. It should also be appreciated that the intramedullary fixation assembly 800 is locked at the fixed angle after insertion of the same into bone. The intramedullary fixation assembly 800 translates compression applied to bone fragments by the tapered screw member 810 and the lag screw member 815 into uniform compression through multi-point fixation.

Figure 10:
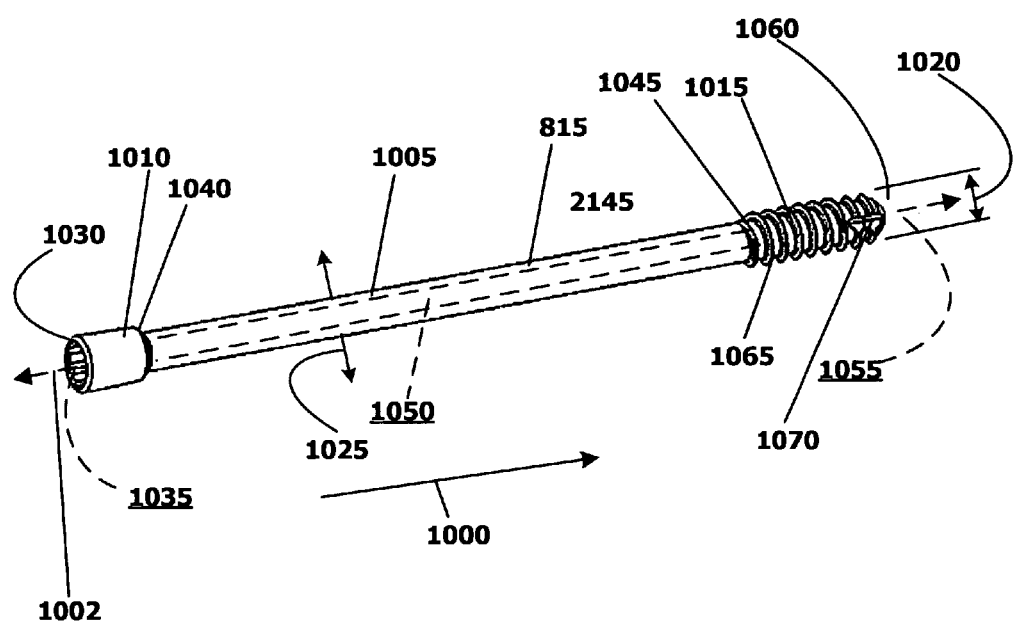
FIG. 10 is a perspective view of the lag screw member used in the intramedullary fixation assembly shown in FIGS. 8-9 according to the alternate embodiment of the invention.

As shown in FIG. 10, lag screw member 815 is generally cylindrical in shape and has a first smooth exterior portion 1005 that extends from first bulbous portion 1010 to a second threaded portion 1015. Additionally, bulbous portion 1010 has a taper, such as a Morse taper, with a width that decreases from end 1030 in direction 1000. The Morse taper allows for a locked interference fit with tapered aperture 1130 (shown in FIG. 11) when tapered bulbous portion 1010 resides within tapered aperture 1130, which will be shown and described below. Moreover, tapered bulbous portion 1010 is generally cylindrical in shape and has a generally hexagonal-shaped aperture 1035 aligned along axis 1002 traversing the longitudinal length of bulbous portion 1010. However, a star-shaped aperture, a square-shaped aperture, or any other shaped aperture may be utilized without departing from the scope of the invention. Aperture 1035 is provided to transmit torque from bulbous portion 1010 to threaded portion 1015 as bulbous portion 1010 is rotated in a direction that causes a corresponding rotation of threaded portion 1015.

Further, lag screw member 815 has a first smooth exterior portion 1005 that has a uniform diameter 1025 from first end 1040 to second end 1045. Portion 1005 includes an internal aperture 1050 aligned along axis 1002 that traverses the longitudinal length of portion 1005 in direction 1000. Further, portion 1005 terminates into a threaded portion 1015.

Threaded portion 1015 includes an internal aperture 1055 aligned along axis 1002 that longitudinally traverses threaded portion 1015. Internal aperture 1055 being aligned on the same axis 1002 as apertures 1035 and 1055 cooperatively form a continuous opening (i.e., a cannula) from end 1030 of bulbous portion 1010 to end 1060 of threaded portion 1015. The continuous opening or cannula is provided to interact with a guide wire (not shown) by receiving the guide wire within the continuous opening to help guide and position the lag screw member 815 during insertion of the lag screw member 815. In other non-limiting embodiments, the lag screw member 815 may be provided without apertures 1050 and 1055 (i.e., the lag screw member 815 is solid).

Furthermore, threaded portion 1015 has a plurality of circular threads, such as threads 1065, which are circumferentially (i.e., spirally) disposed on the external surface of threaded portion 1015. Threaded portion 1015 has a diameter 1020 that is substantially the same as diameter 1025 of portion 1005. Threaded portion 1015 may also be provided with a self-tapping leading edge 1070 to provide portion 1015 with the ability to remove bone material during insertion of lag screw member 815 into bone. It should be appreciated that the length of the lag screw member 815 may be selected of varying lengths to allow a surgeon to fuse different joints in the human body. It should be appreciated that the lag screw member 815 may be positioned at one angle inside the tapered screw member 810. Also, lag screw member 815 may be coated with an osteoconductive material, such as, for example, plasma spray or other similar types of porous materials that is capable of supporting or encouraging bone ingrowth into this material.

Figure 11:
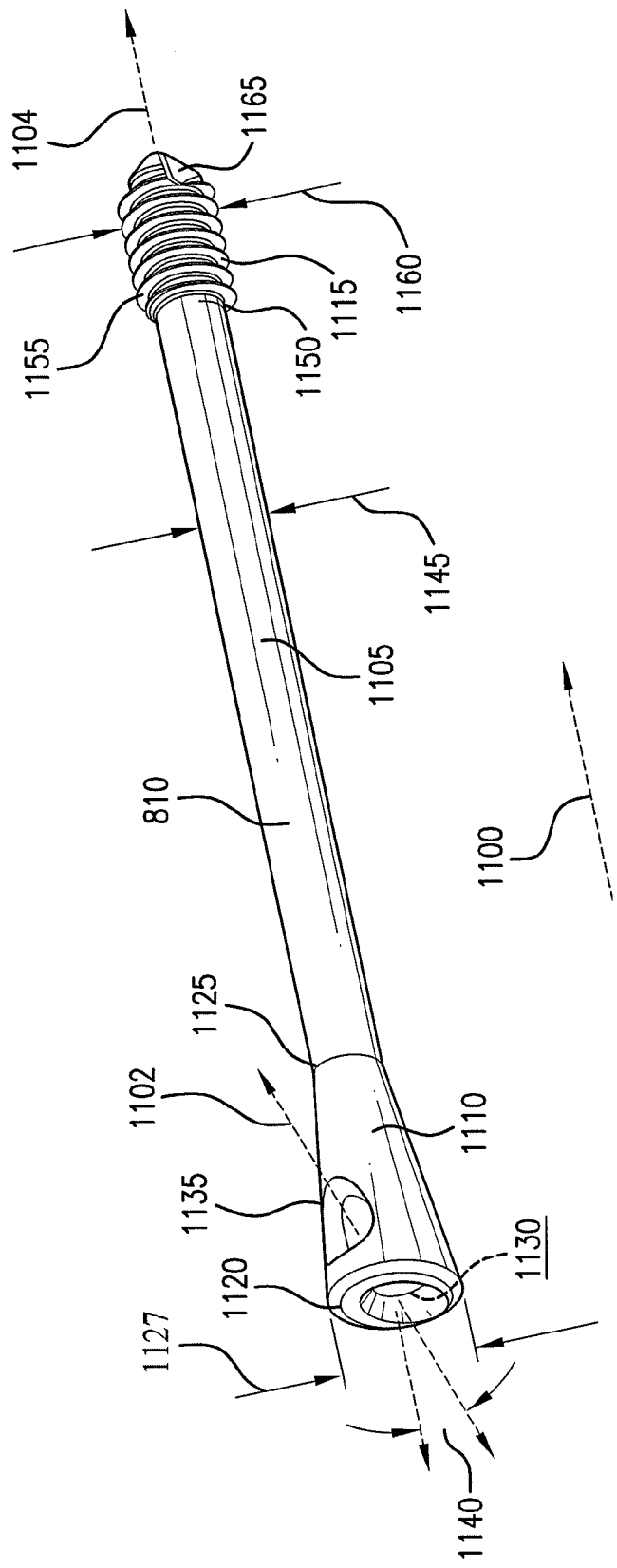
FIG. 11 is a perspective view of the tapered screw member used in the intramedullary fixation assembly shown in FIGS. 8-9 according to the alternate embodiment of the invention.

As shown in FIG. 11, tapered screw member 810 is generally cylindrical in shape and has a smooth exterior portion 1105 that extends from a tapered portion 1110 to a threaded portion 1115. Tapered screw member 810 is aligned along longitudinal axis 1104, which is longitudinally coextensive with length of tapered screw member 810.

Further, tapered portion 1110 is generally tubular in shape and tapers from end 1120 to end 1125 (i.e. end 1120 has a diameter 1127 that decreases slightly in diameter from end 1120 in direction 1100). Further, first end 1120 has a tapered aperture 1130, which traverses tapered portion 1110 along axis 1102, which causes tapered aperture 1130 to emanate from surface 1135. Axis 1102 is offset from longitudinal axis 1104 at an angle 1140. Moreover, tapered portion 1110 has a generally hexagonal-shaped aperture contained within portion 1110, which is aligned along axis 1104 and is provided to receive an instrument (not shown) for applying torque to tapered screw member 810. In other non-limiting embodiments, a star-shaped aperture, a square-shaped aperture, or any other shaped aperture may be utilized without departing from the scope of the invention. With tapered aperture 1130 being aligned along axis 1102, tapered aperture 1130 forms a fixed angle 1140 with longitudinal axis 1145. Fixed angle 1140 determines the angle for fixation of tapered screw member 810 with respect to lag screw member 815 (shown in FIG. 10). It should be appreciated that fixed angle 1140 may be any angle less than 90 degrees to allow a surgeon the flexibility of determining the angle for internal fixation of bones in the human body. It should also be appreciated that tapered aperture 1130 when combined with tapered bulbous portion 1010, shown in FIG. 10, creates a locked interference fit between tapered screw member 810 and lag screw member 815.

Further, tapered screw member 810 has a smooth exterior portion 1105 that has a uniform diameter 1145 from end 1125 to end 1150. Tapered screw member 810 is generally solid, however, in other non-limiting embodiments, screw member 810 may be cannulated. Further, portion 1105 terminates into a threaded portion 1115. Threaded portion 1115 is generally solid and includes a plurality of circular threads, such as threads 1155, which are circumferentially (i.e., spirally) disposed on the external surface of threaded portion 1115. Threaded portion 1115 has a diameter 1160 that is substantially the same as diameter 1145 of portion 1105. Threaded portion 1115 may also be provided with a self-tapping leading edge 1165 to provide portion 1115 with the ability to remove bone material during insertion of tapered screw member 810 into bone. It should be appreciated that the length of the tapered screw member 810 may be selected of varying lengths to allow a surgeon to fuse different joints in the human body. It should be appreciated that tapered screw member 810 may be coated with an osteoconductive material, such as, for example, plasma spray or other similar types of porous materials that is capable of supporting or encouraging bone ingrowth into this material.

Figure 12:
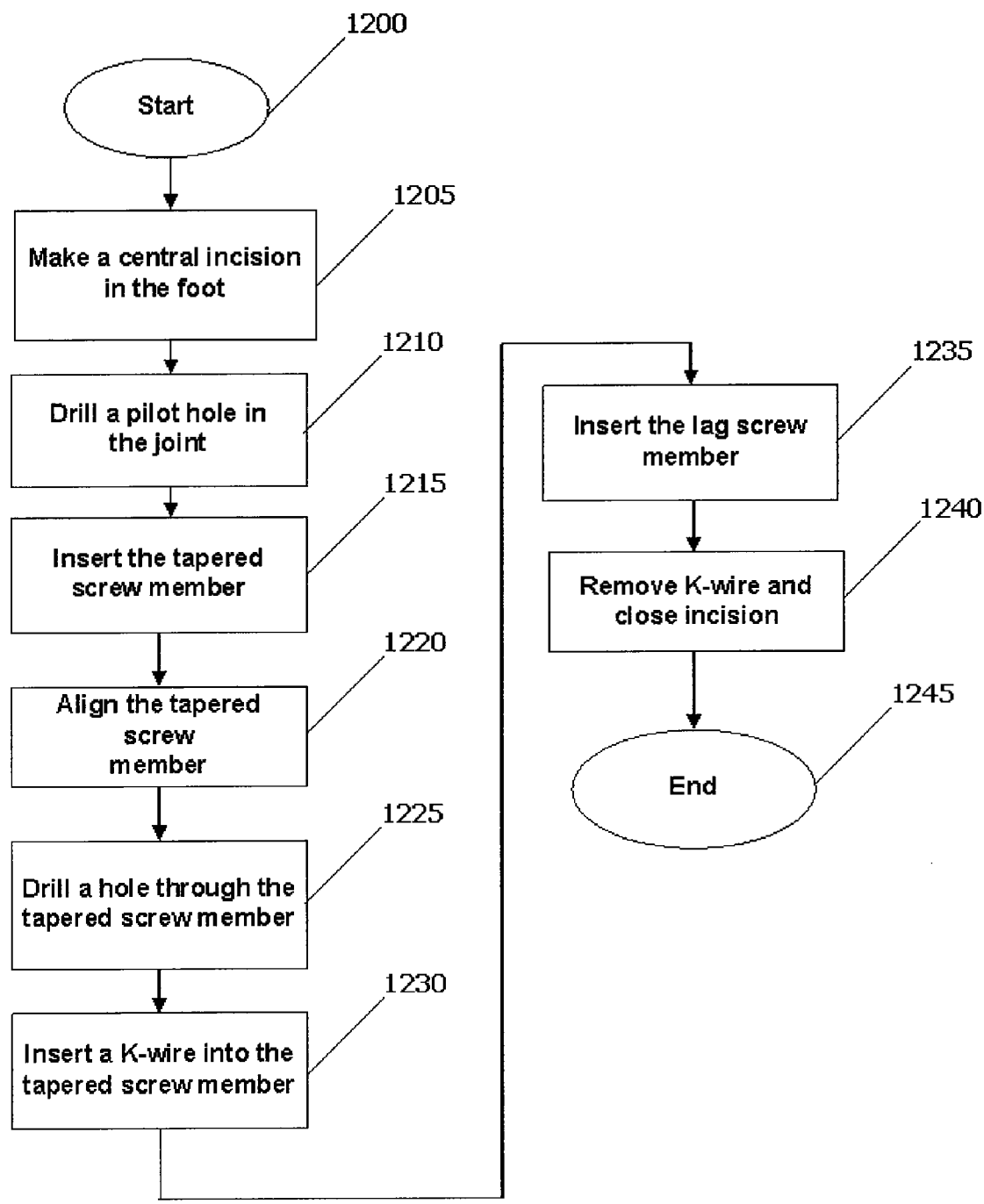
FIG. 12 is a flow chart illustrating the method of coupling the intramedullary fixation assembly shown in FIG. 8-9 to bones in a patient's foot according to the alternate embodiment of the invention.

As shown in FIGS. 8 and 12, the intramedullary fixation assembly 800 may be utilized to apply compression, for example to the bones in a human foot through an acute angle fixation of the tapered screw member 810 to the lag screw member 815. As shown, the method starts in step 1200 and proceeds to step 1205, whereby a central incision is made in the hind-foot region of foot 805. Next, in step 1210, a pilot hole is drilled into the calcaneus 820 and the cuboids 830 bones. In this step, a countersink drill is inserted and a cannulated drill or guide wire is used to pre-drill the hole through the joints selected for fusion. Next, in step 1215, tapered screw member 810 is inserted into the intraosseous intramedullary canal (not shown) of the calcaneus 820. In other non-limiting embodiments, the tapered screw member 810 may be inserted by impaction, by press fit, by reaming a hole in the intramedullary canal (not shown) or substantially any other similar strategy or technique.

Next, in step 1220, the final position of the tapered screw member 810 is aligned so that the coupling of the lag screw member 815 forms a predetermined angle with the tapered screw member 810. In step 1225, align a guide through tapered aperture 1130 at surface 1135 and pre-drill a hole through the joint substantially along axis 1102. Next, in step 1230, insert a K-wire (not shown) into the pre-drilled hole and into the tapered screw member 810 so that the K-wire makes an acute angle with the tapered screw member 810. Next, in step 1235, the lag screw member 815 is rotated and inserted over the K-wire and into the calcaneus bone 820 so that the K-wire guides the lag screw member 815. The K-wire, in assisting the lag screw member 815, penetrates end 1060 and emanates from end 1030. In some non-limiting embodiments, the lag member 815 may be inserted by impaction, by press fit, or substantially any other similar strategy or technique. Next, in step 1240, the K-wire is removed and the incision is closed. The method ends in step 1245.

Figure 13:
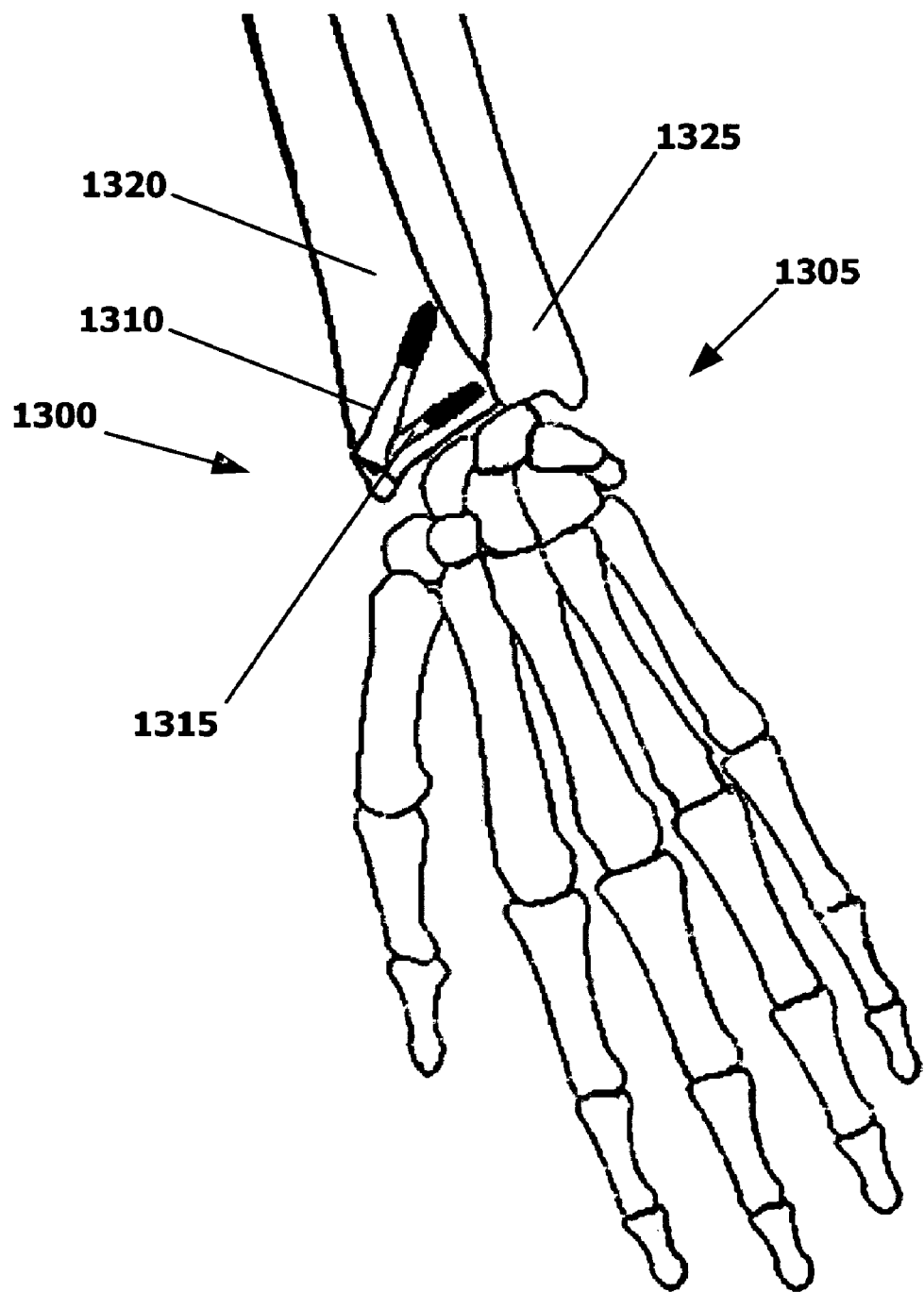
FIG. 13 is a perspective view of an assembled intramedullary fixation assembly inserted into the bones of a patient's hand according to an alternate embodiment of the invention.

In an alternate embodiment, as shown in FIG. 13, an intramedullary fixation assembly 1300 is provided for the internal fixation of bones in a human hand 1305. Particularly, the intramedullary fixation assembly 1300 is substantially the same as the intramedullary fixation assembly 800 of the embodiment shown and described in FIG. 8. The intramedullary fixation assembly 1300 includes a tapered screw member 1310 forming a fixed acute angle with the lag screw member 1315. The fixed acute angle is predetermined and the angle may be selected up to 90 degrees by, in one example, a surgeon to provide for the internal fixation of the bones in the human hand 1305, such as for example the radius 1320 and ulna 1325.

Figure 14:
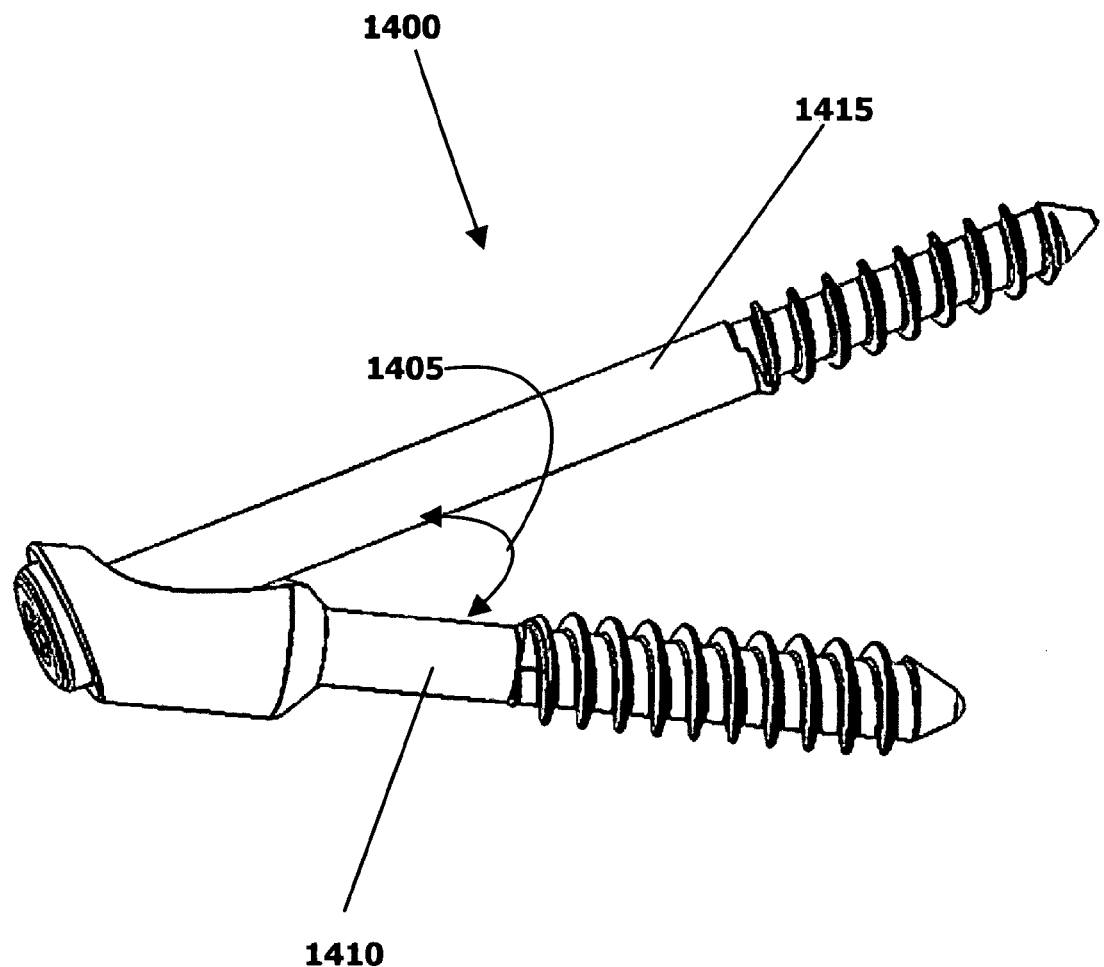
FIG. 14 is a perspective view of the intramedullary fixation assembly shown in FIG. 13 according to the alternate embodiment of the invention.

In another alternate embodiment, as shown in FIG. 14, an intramedullary fixation assembly 1400 may be provided to vary the acute angle between 0 and 90 degrees after insertion of the intramedullary fixation assembly 1400. Particularly, the intramedullary fixation assembly 1400 comprises a polyaxial screw member 1410 coupled to a lag screw member 1415 and forming an acute angle 1405 between the two members 1410 and 1415. The angle 1405 between the polyaxial screw member 1410 and the lag screw member 1415 causes the intramedullary fixation assembly 1400 to "hook" into the bone segments and translates the compression applied to bone fragments across the members 1410 and 1415. It should be appreciated that the intramedullary fixation assembly 1400 may be provided at several lengths for the internal fixation of a variety of bone sizes in the human body. It should also be appreciated that in one non-limiting embodiment, the intramedullary fixation assembly 1400 may be made from a Titanium material, although, in other non-limiting embodiments, the intramedullary fixation assembly 1400 may be made from SST, PEEK, NiTi, Cobalt chrome or other similar types of materials.

Figure 15:
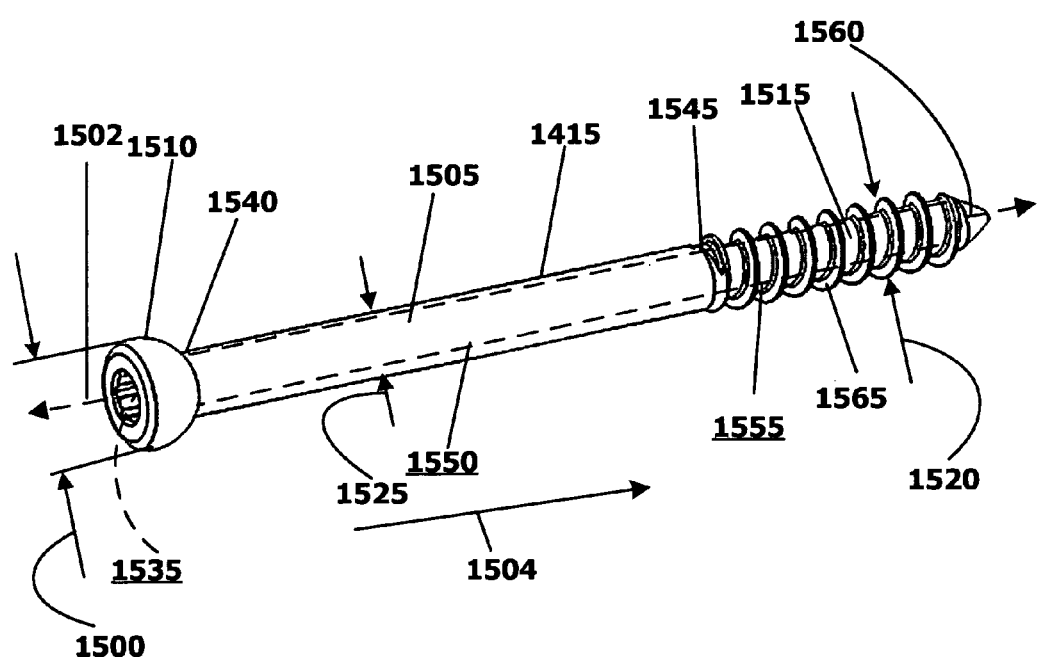
FIG. 15 is a perspective view of the lag screw member used in the intramedullary fixation assembly shown in FIG. 14 according to the alternate embodiment of the invention.

As shown in FIG. 15, lag screw member 1415 is generally cylindrical in shape and has a first smooth exterior portion 1505 that extends from first bulbous portion 1510 to a second threaded portion 1515. Bulbous portion 1510 is generally semispherical in shape and has a diameter 1500 that is slightly larger than the internal diameter of aperture 1630 (shown in FIG. 16), which is provided to receive bulbous portion 1510. The bulbous portion 1510 resides within the internal aperture 1630 (shown in FIG. 16) and provides for rotational movement of both the polyaxial screw member 1410 and the lag screw member 1415 at various angles between 0 and 90 degrees after insertion of the intramedullary fixation assembly 1400. Also, bulbous portion 1510 has a generally hexagonal-shaped aperture 1535 aligned along axis 1502 traversing the longitudinal length of bulbous portion 1510. In other non-limiting embodiments, a star-shaped aperture, a square-shaped aperture, or any other shaped aperture may be utilized without departing from the scope of the invention. Aperture 1535 is provided to transmit torque from bulbous portion 1510 to threaded portion 1515 as bulbous portion 1510 is rotated in a direction that causes a corresponding rotation of threaded portion 1515. It should also be appreciated that axis 1502 is longitudinally coextensive with the length of lag screw member 1415.

Further, lag screw member 1415 has a first smooth exterior portion 1505 of a uniform diameter 1525 from first end 1540 to second end 1545. Portion 1505 includes an internal aperture 1550 aligned along axis 1502 that traverses the longitudinal length of portion 1505 along direction 1504. Further, portion 1505 terminates into the threaded portion 1515. Threaded portion 1515 also includes an internal aperture 1555 aligned along axis 1502 that longitudinally traverses threaded portion 1515. Internal aperture 1555 being aligned along the same axis 1502 as apertures 1535 and 1550 to cooperatively form a continuous opening (i.e., a cannula) from bulbous portion 1510 to end 1560 of threaded portion 1515. The continuous opening or cannula is provided to interact with a guide wire (not shown) by receiving the guide wire within the continuous opening to help guide and position the lag screw member 1415 during insertion into bone. In other non-limiting embodiments, the lag screw member 1415 may be provided without apertures 1550 and 1555 (i.e., the lag screw member 1415 is non-cannulated or solid).

Furthermore, threaded portion 1515 has a plurality of circular threads, such as threads 1565, which are circumferentially (i.e., spirally) disposed on the external surface of threaded portion 1515. Threaded portion 1515 has a diameter 1520 that is substantially the same as diameter 1525 of portion 1505. Threaded portion 1515 may also be provided with a self-tapping leading edge (not shown) to provide portion 1515 with the ability to remove bone material during insertion of lag screw member 1415 into bone. It should be appreciated that the length of the lag screw member 1415 may be selected of varying lengths to allow a surgeon to fuse different joints in the human body. Also, lag screw member 1415 may be coated with an osteoconductive material, such as, for example, plasma spray or other similar types of porous materials that is capable of supporting or encouraging bone ingrowth into this material.

Figure 16:
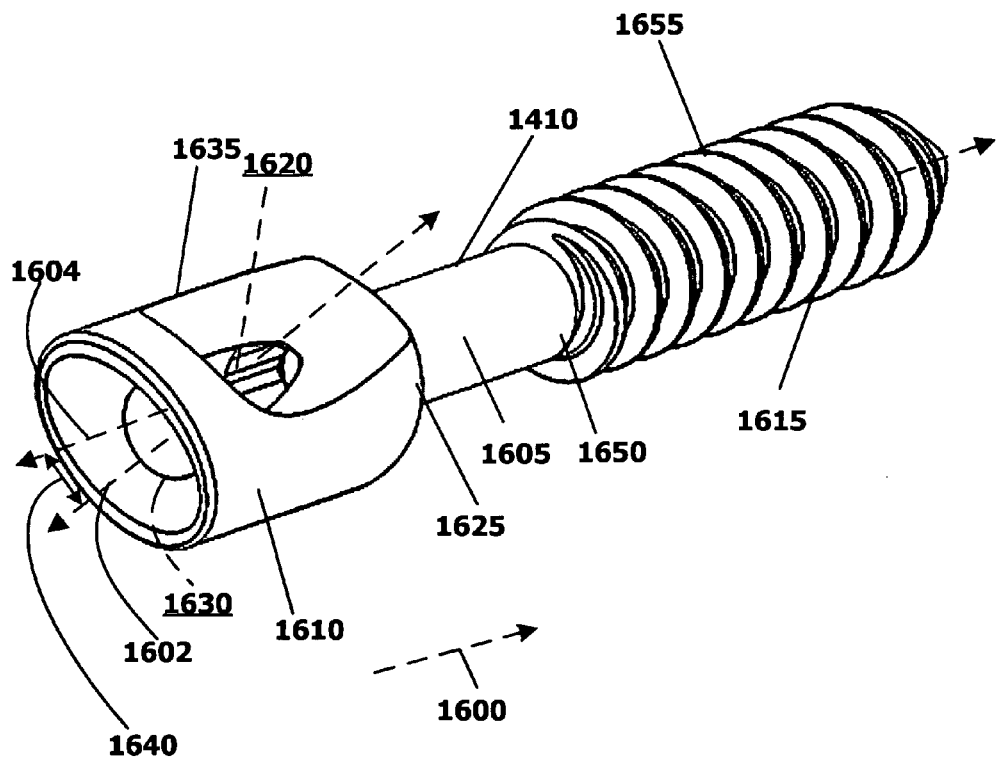
FIG. 16 is a perspective view of the polyaxial screw member used in the intramedullary fixation assembly shown in FIG. 14 according to the alternate embodiment of the invention.

As shown in FIG. 16, polyaxial screw member 1410 is generally cylindrical in shape and has a smooth exterior portion 1605 that extends from portion 1610 to a threaded portion 1615. Polyaxial screw member 1410 is aligned along longitudinal axis 1604, which is longitudinally coextensive with length of polyaxial screw member 1410.

Further, portion 1610 is generally tubular in shape having a uniform diameter, which is slightly larger than diameter of aperture 1630 causing portion 1610 to abut the interior surface of portion 1610 at aperture 1630. However, in other non-limiting embodiments, portion 1610 may be tapered going from a larger diameter to a smaller diameter as we traverse portion 1610 along direction of axis 1600. Further, portion 1610 has a plurality of apertures 1620 and 1630 of dissimilar diameters. Aperture 1630 is a through aperture and is tapered along axis 1602, causing aperture 1630 to emanate from surface 1635. On the other hand, aperture 1620 is longitudinally disposed along axis 1604 and has a generally hexagonal shaped aperture, although in other non-limiting embodiments, a star-shaped aperture, a square-shaped aperture, or any other shapes aperture may be utilized. Aperture 1630 is offset from axis 1604 at an angle 1640. Angle 1640 determines the angle for rotation of lag screw member 1415 when bulbous portion 1510 (shown in FIG. 15) resides in aperture 1630 with lag screw member 1415 rotating angularly around axis 1602. It should be appreciated that angle 1640 may be any angle less than 90 degrees to allow a surgeon the flexibility of fixing the rotation of polyaxial screw member 1410 and lag screw member 1415.

Further, polyaxial screw member 1410 has a smooth exterior portion 1605 having a uniform diameter from end 1625 to end 1650. The diameter of exterior portion 1605 is smaller than the diameter of aperture 1630. Polyaxial screw member 1410 is generally solid, however, in another non-limiting embodiment, polyaxial screw member 1410 may be cannulated. Further, portion 1605 terminates into a threaded portion 1615. Threaded portion 1615 is generally solid and includes a plurality of circular threads, such as threads 1655, circumferentially (i.e., spirally) disposed on the external surface of threaded portion 1615. Threaded portion 1615 has a uniform diameter that is slightly larger than the diameter of portion 1605. However, in other non-limiting embodiments, the respective diameters of portions 1605 and 1615 may be substantially the same. Threaded portion 1615 may also be provided with a self-tapping leading edge (not shown) to provide portion 1615 with the ability to remove bone material during insertion of polyaxial screw member 1410 into bone. It should be appreciated that the length of the polyaxial screw member 1410 may be selected of varying lengths to allow a surgeon to fuse different joints in the human body. It should be appreciated that polyaxial screw member 1410 may be coated with an osteoconductive material, such as, for example, plasma spray or other similar types of porous materials that is capable of supporting or encouraging bone ingrowth into this material.

Figure 17:
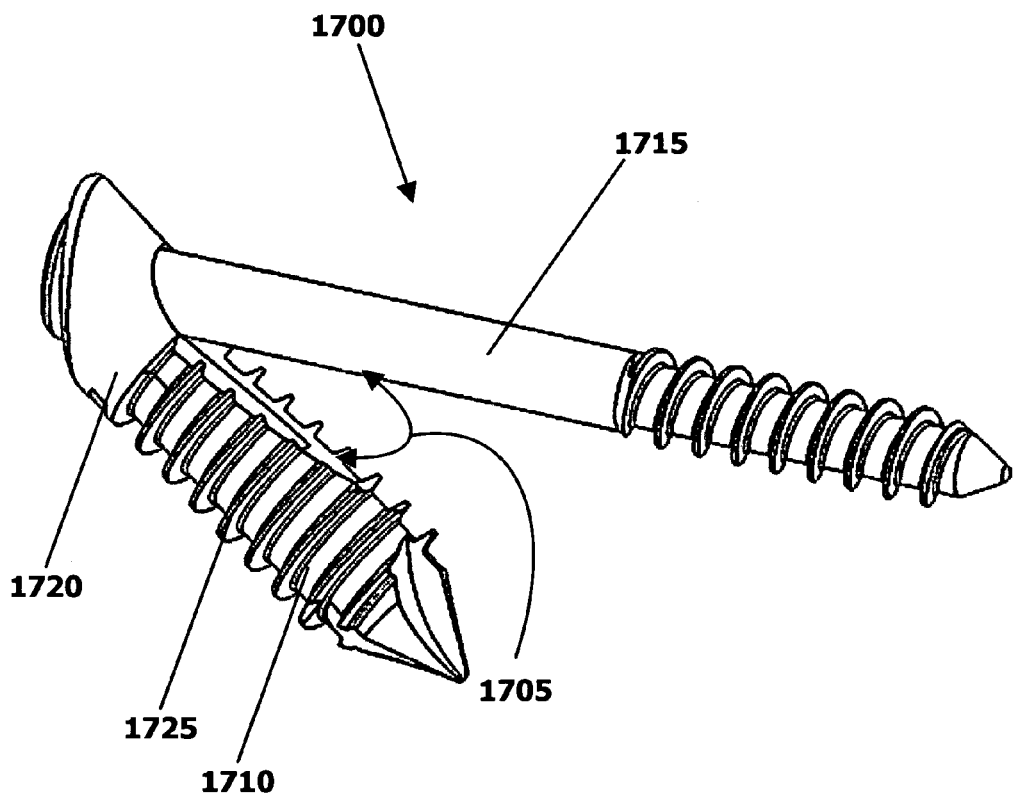
FIG. 17 is a perspective view of an assembled intramedullary fixation assembly according to an alternate embodiment of the invention.

In another alternate embodiment, as shown in FIG. 17, length of the polyaxial screw member 1710 may be varied in order to accommodate the intramedullary fixation assembly 1700 in bones of various sizes. Particularly, the polyaxial screw member 1710 includes a smooth end portion 1720 coupled directly to a threaded portion 1725, and includes an angled aperture to vary the angle 1705 that is formed between the polyaxial screw member 1710 and the lag screw member 1715. In all other respects, the intramedullary fixation assembly 1700 is substantially similar to the intramedullary fixation assembly 1400 as was shown and described in FIG. 14.

Figure 18:
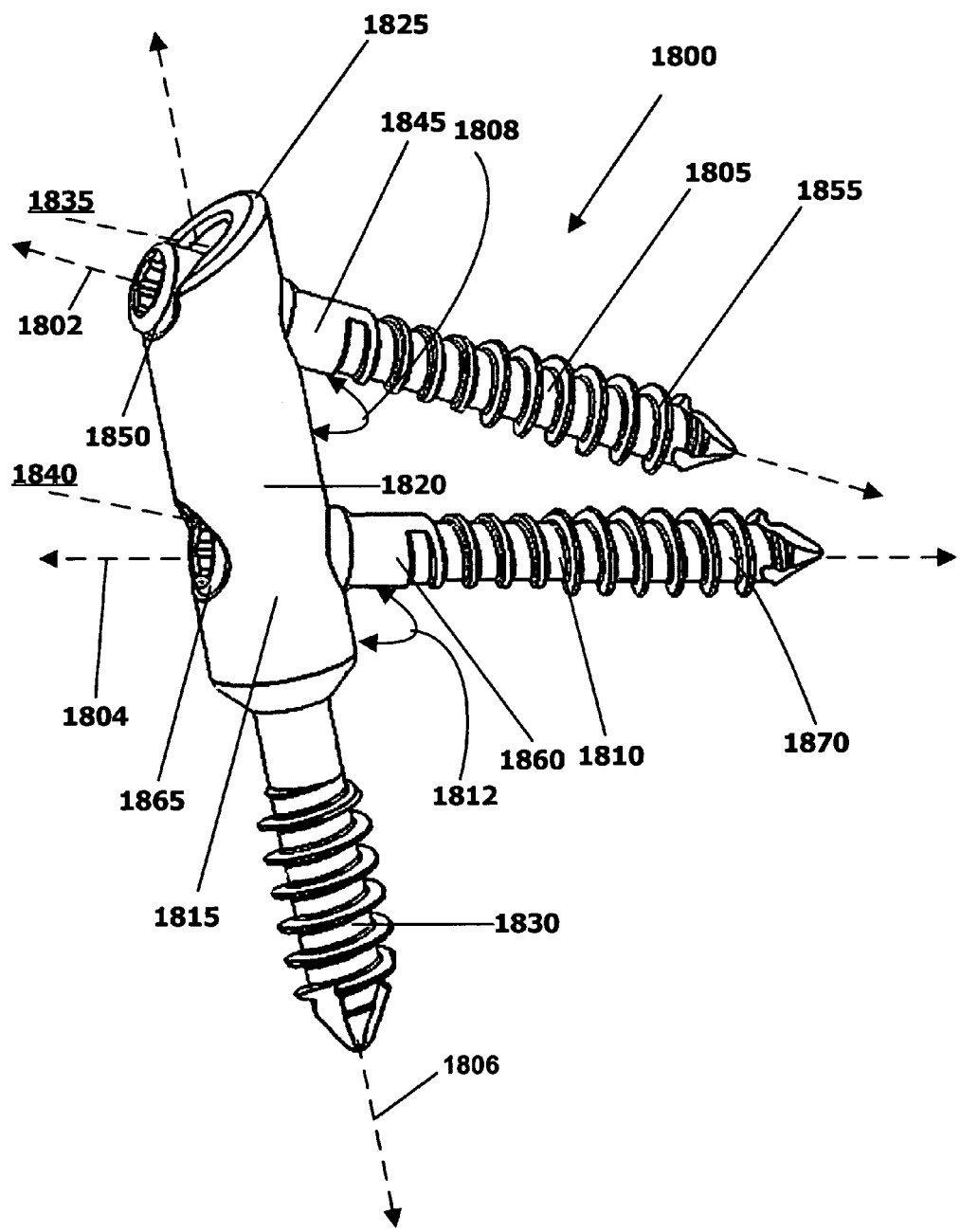
FIG. 18 is a perspective view of an assembled intramedullary fixation assembly having a plurality of lag screw members according to an alternate embodiment of the invention.

In another alternate embodiment, as shown in FIG. 18, an intramedullary fixation assembly 1800 having a plurality of lag screw members 1805 and 1810 coupled to a tapered screw member 1815 is provided in order to apply compression at multiple points on the bone fragment surface. Particularly, the lag screw members 1805 and 1810, and the tapered screw member 1815 are substantially similar to the lag screw member 815 and tapered screw member 810 respectively shown and described in the embodiment of FIGS. 8-11. Each of the lag screw members 1805 and 1810 forms q fixed acute angle with the tapered screw member 1815, with these acute angles being predetermined by, for example, a surgeon to fix the bones in a human body.

As shown, tapered screw member 1815 is generally cylindrical in shape and has a smooth exterior portion 1820 that extends longitudinally along axis 1806 from end 1825 to a threaded portion 1830. Further, end 1825 has a tapered aperture 1835, which is aligned on axis 1802 and forms a fixed angle 1808 with axis 1806, which passes longitudinally though tapered screw member 1815. Fixed angle 1808 determines the angle for fixation of tapered screw member 1810 with respect to lag screw member 1805. Also, tapered screw member 1815 has a second tapered aperture 1840, aligned along axis 1804 and forms a fixed angle 1812 with axis 1804. The fixed angle 1812 determines the angle for fixation of lag screw member 1810 with tapered screw member 1815. It should be appreciated that fixed angles 1808 and 1812 may be any angle less than 90 degrees to allow a surgeon the flexibility of determining the angle for internal fixation of bones in the human body. It should also be appreciated that tapered screw member 1815 creates a locked interference fit with each of the lag screw members 1805 and 1810.

Further, tapered screw member 1815 has a smooth exterior portion 1820 having a uniform diameter from end 1825 to threaded portion 1830. Tapered screw member 1815 is generally solid, however, in another non-limiting embodiment, screw member 1815 may be cannulated. Further, threaded portion 1830 is generally solid and includes a plurality of circular threads circumferentially disposed on the external surface of threaded portion 1830. Threaded portion 1830 may also be provided with a self-tapping leading edge to provide portion 1830 with the ability to remove bone material during insertion of tapered screw member 1815 into bone. It should be appreciated that the length of the tapered screw member 1815 may be selected of varying lengths to allow a surgeon to fuse different joints in the human body. It should be appreciated that tapered screw member 1815 may be coated with an osteoconductive material, such as, for example, plasma spray or other similar types of porous materials that is capable of supporting or encouraging bone ingrowth into this material.

Also as shown in FIG. 18, each of the respective lag screw members 1805 and 1810 are substantially similar to the lag screw member of the embodiment shown and described in FIG. 10. Particularly, lag screw member 1805 is generally cylindrical in shape and has a first smooth exterior portion 1845 that extends from bulbous portion 1850 to a threaded portion 1855, while lag screw member 1810 has a smooth exterior portion 1860 that extends from bulbous portion 1865 to threaded portion 1870. Additionally, each of the bulbous portions 1850 and 1865 have a taper, such as a Morse taper, that provides for a locked interference fit with tapered apertures 1835 and 1840 respectively.

Figure 19:
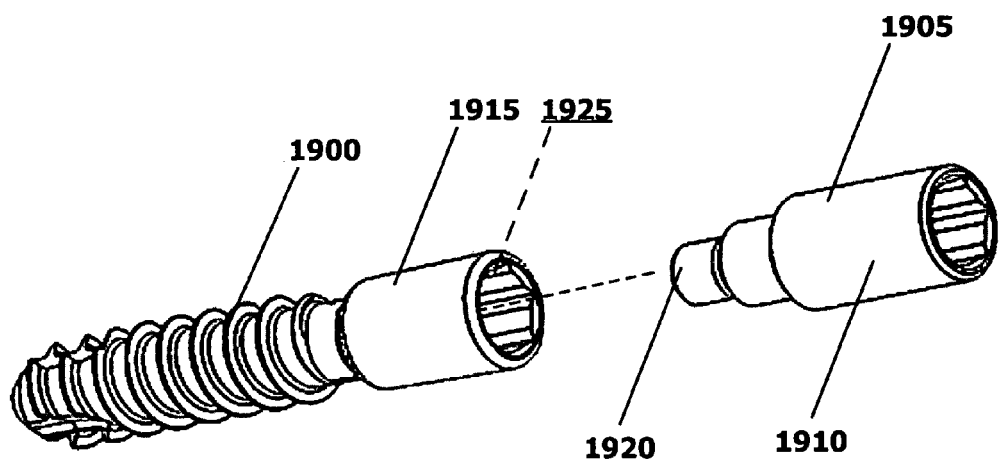
FIG. 19 is an exploded perspective view of a cover member for a lag screw according to an alternate embodiment of the invention.

In an alternate embodiment, as shown in FIG. 19, a lag screw member 1900 may include a cover or plug member 1905. The cover member 1905 includes a first end portion 1910 having substantially the same diameter as end portion 1915. The cover member 1905 also includes a second end portion 1920, which is smaller than the internal diameter of end portion 1915 and which is provided to be received inside aperture 1925 of lag screw member 1900.

It should be appreciated that any number of intramedullary fixation assemblies, such as intramedullary fixation assembly 800, may be inserted into the joints, for example, of the human foot in order to provide for compression of the bones of the foot. It should also be appreciated that the intramedullary fixation assembly 800 is delivered through an incision, thereby reducing the disruption to the plantar tissues while at the same time minimizing the tension on the skin. This allows for improved wound closure, reduced operating room time, reduction in the number of incisions required and reduction in the total length of incisions. It should also be appreciated that the intramedullary fixation assembly 800 may also be utilized to restore any of the other bones in the human body. It should also be appreciated that in other non-limiting embodiments, the intramedullary assembly 800 may be utilized with graft material (i.e., autograft, allograft or other biologic agent).

Figure 20:
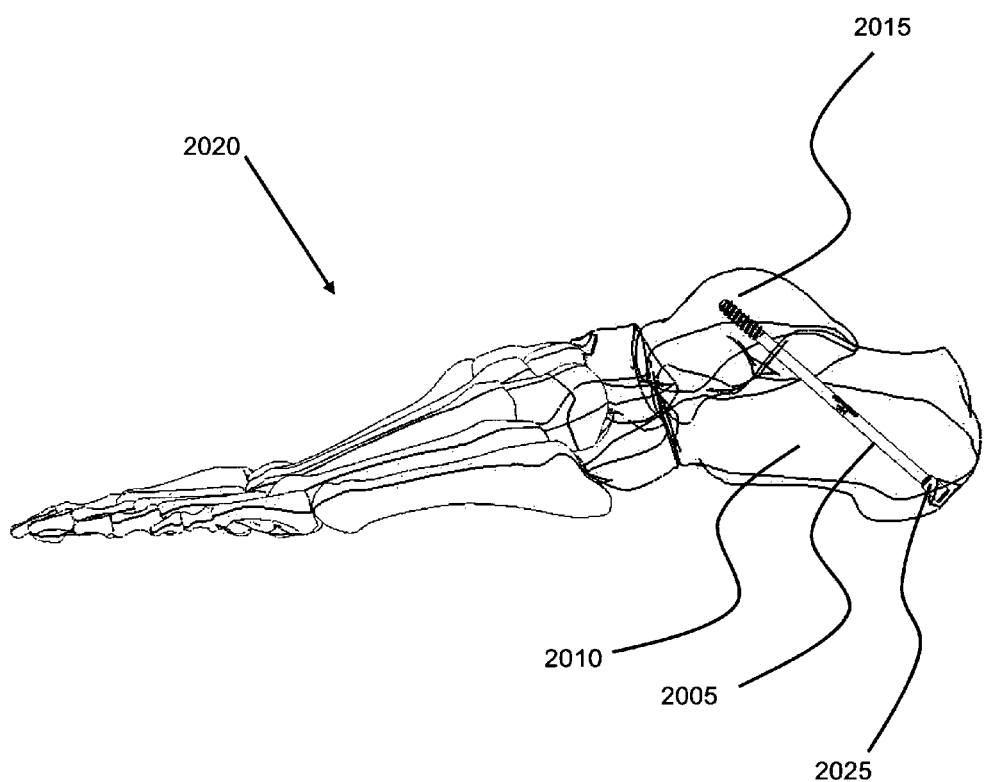
FIG. 20 is a perspective view of a lag screw member inserted into the subtalar joint of a patient's foot according to an alternate embodiment of the invention.
Figure 21A:
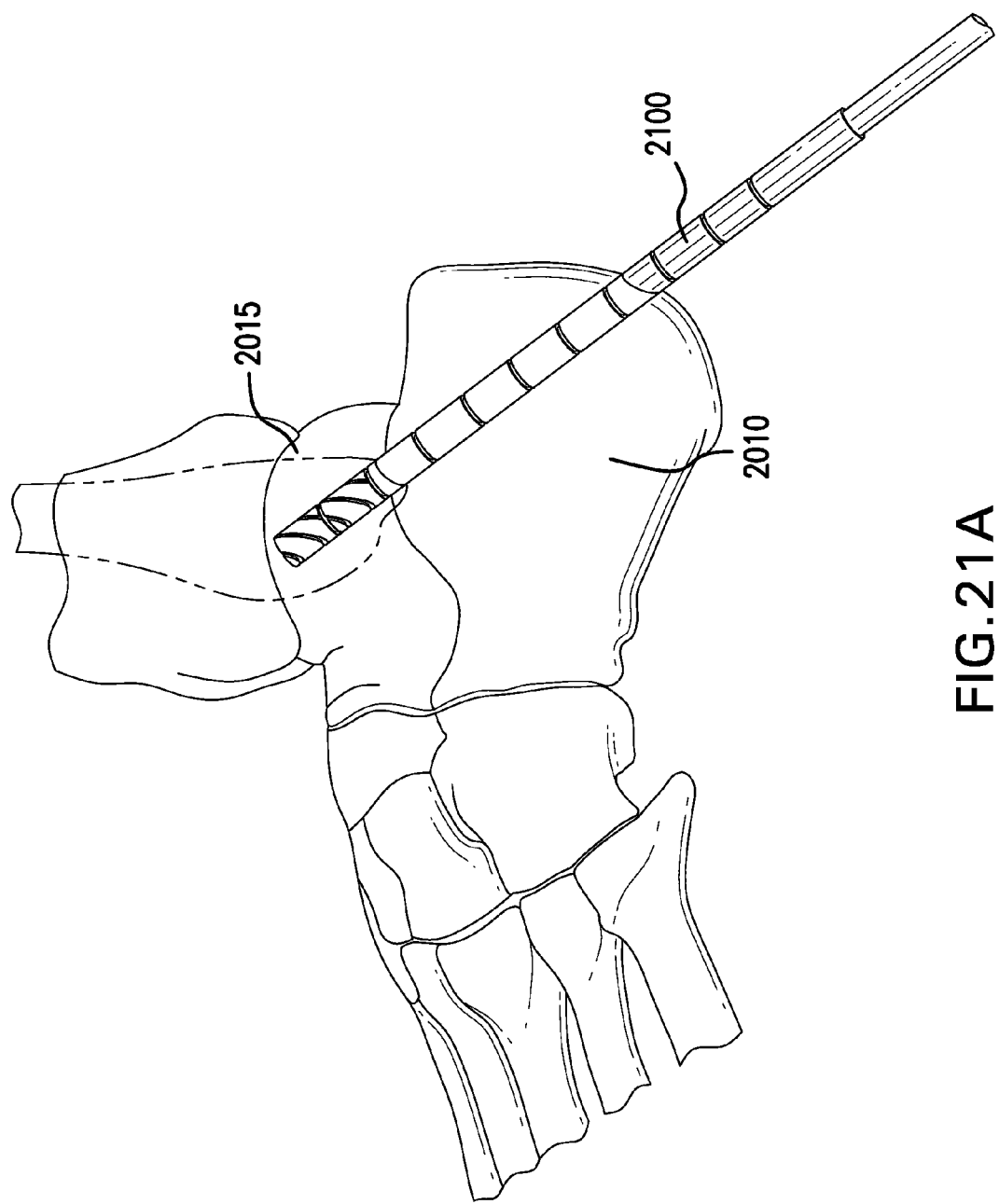
FIG. 21A is a perspective image of the subtalar joint utilized in one step of preparing the subtalar joint for insertion of the lag screw member of FIG. 20 according to the alternate embodiment of the invention.
Figure 21B:
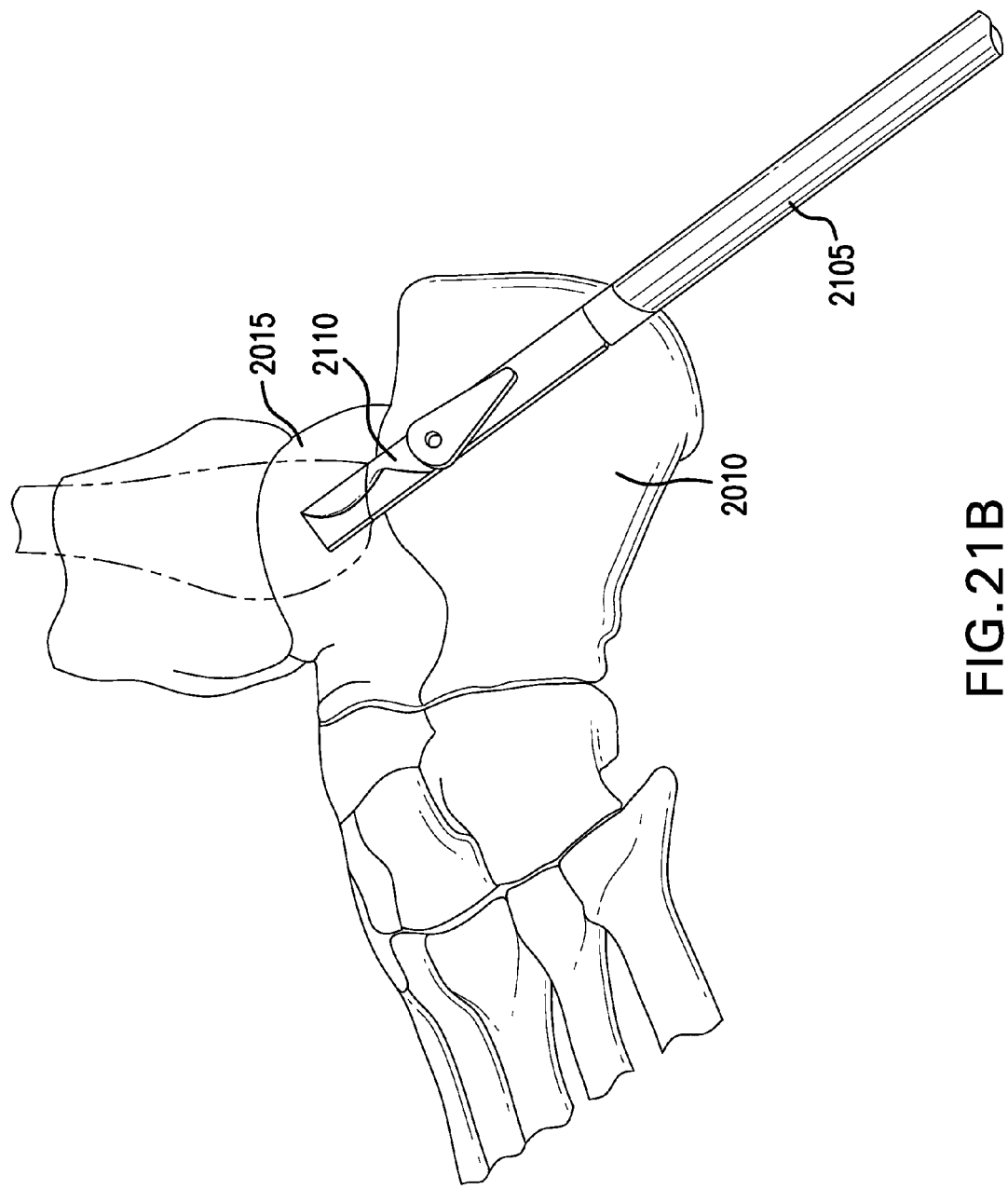
FIG. 21B is a perspective image of the subtalar joint utilized in another step of preparing the subtalar joint for insertion of the lag screw member of FIG. 20 according to the alternate embodiment of the invention.
Figure 21C:
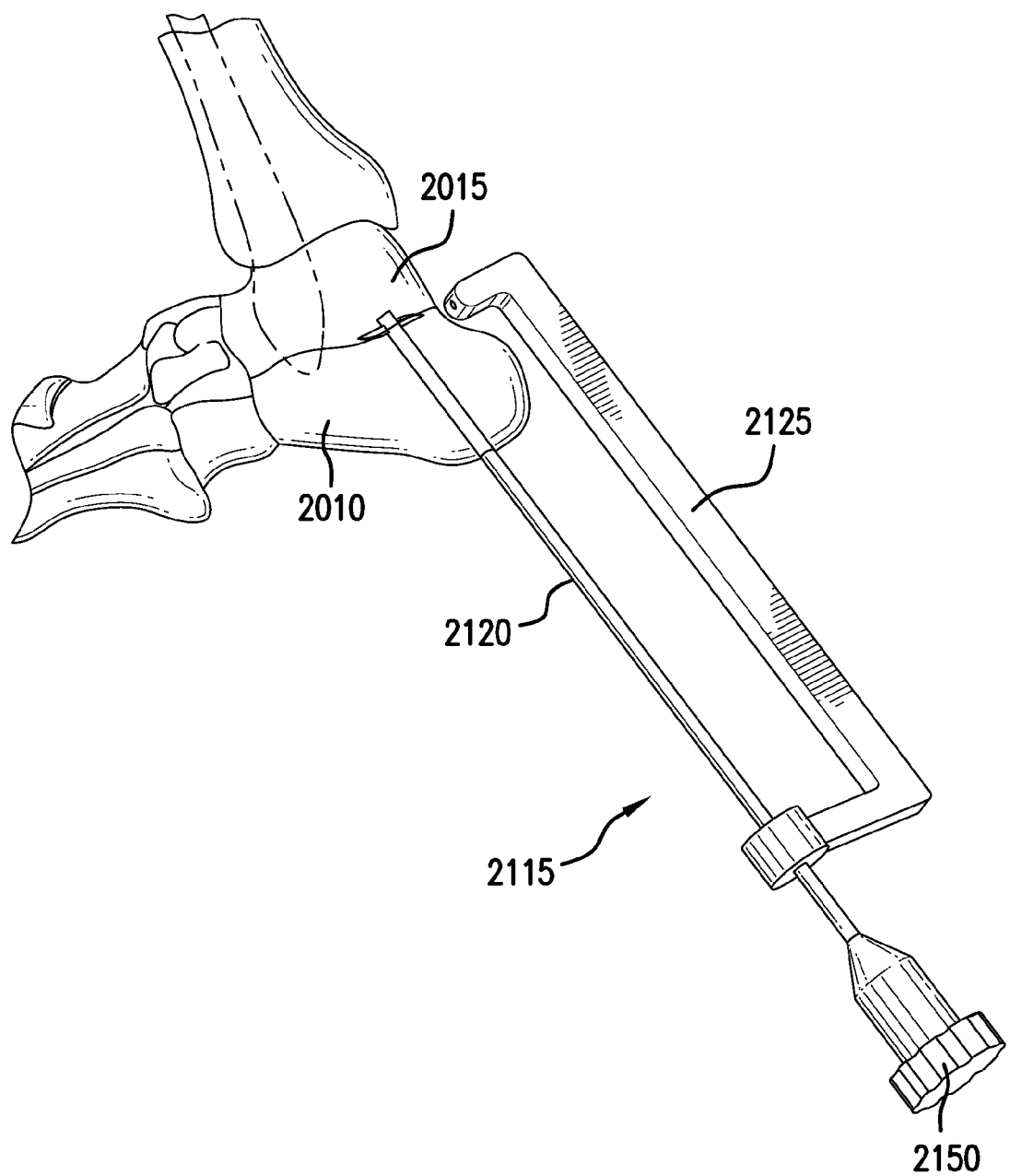
FIG. 21C a perspective image of the subtalar joint in yet another step of preparing the subtalar joint for insertion of the lag screw member of FIG. 20 according to the alternate embodiment of the invention.
Figure 21D:
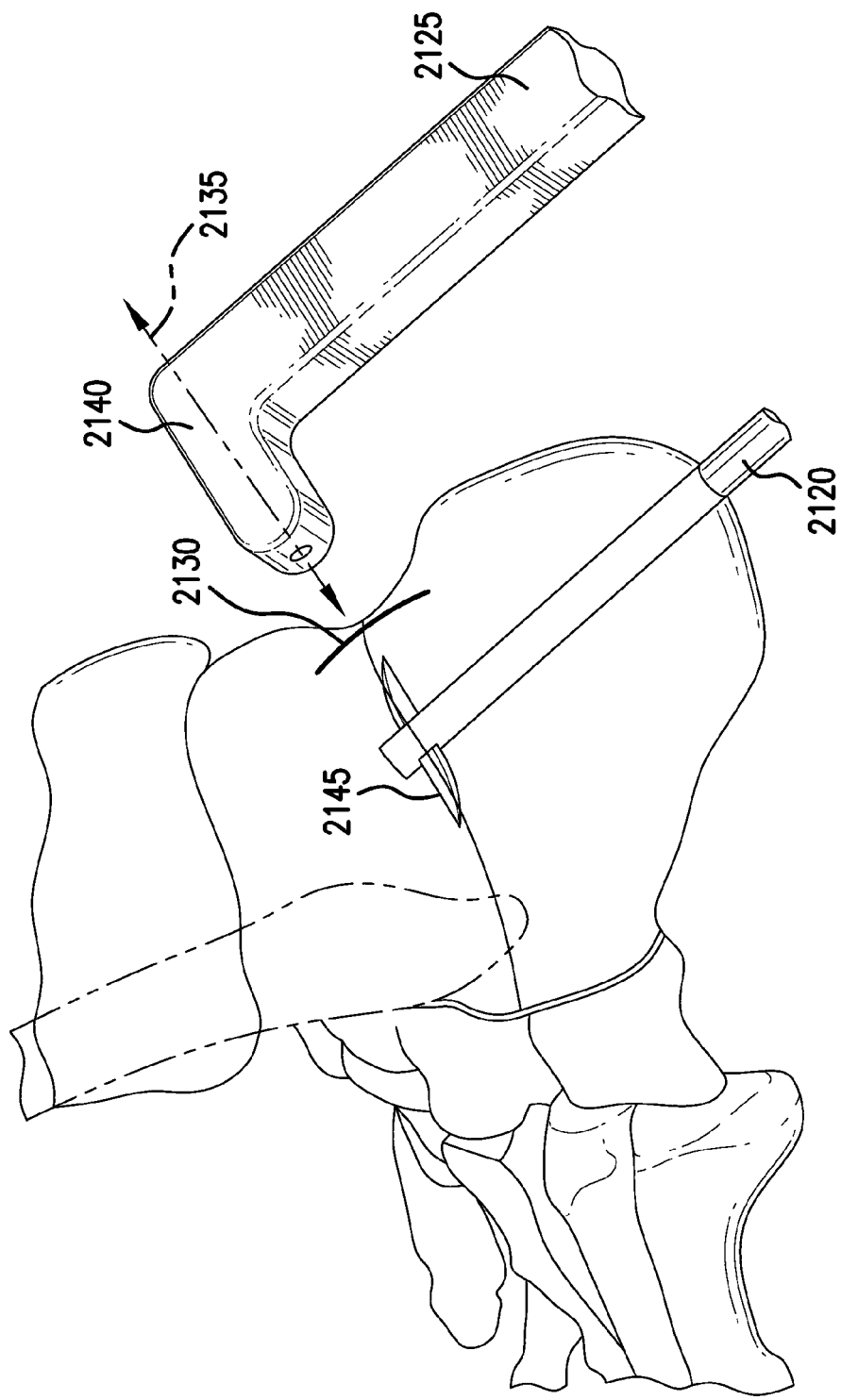
FIG. 21D a perspective image of the subtalar joint in another step of preparing the subtalar joint for insertion of the lag screw member of FIG. 20 according to the alternate embodiment of the invention.
Figure 21E:
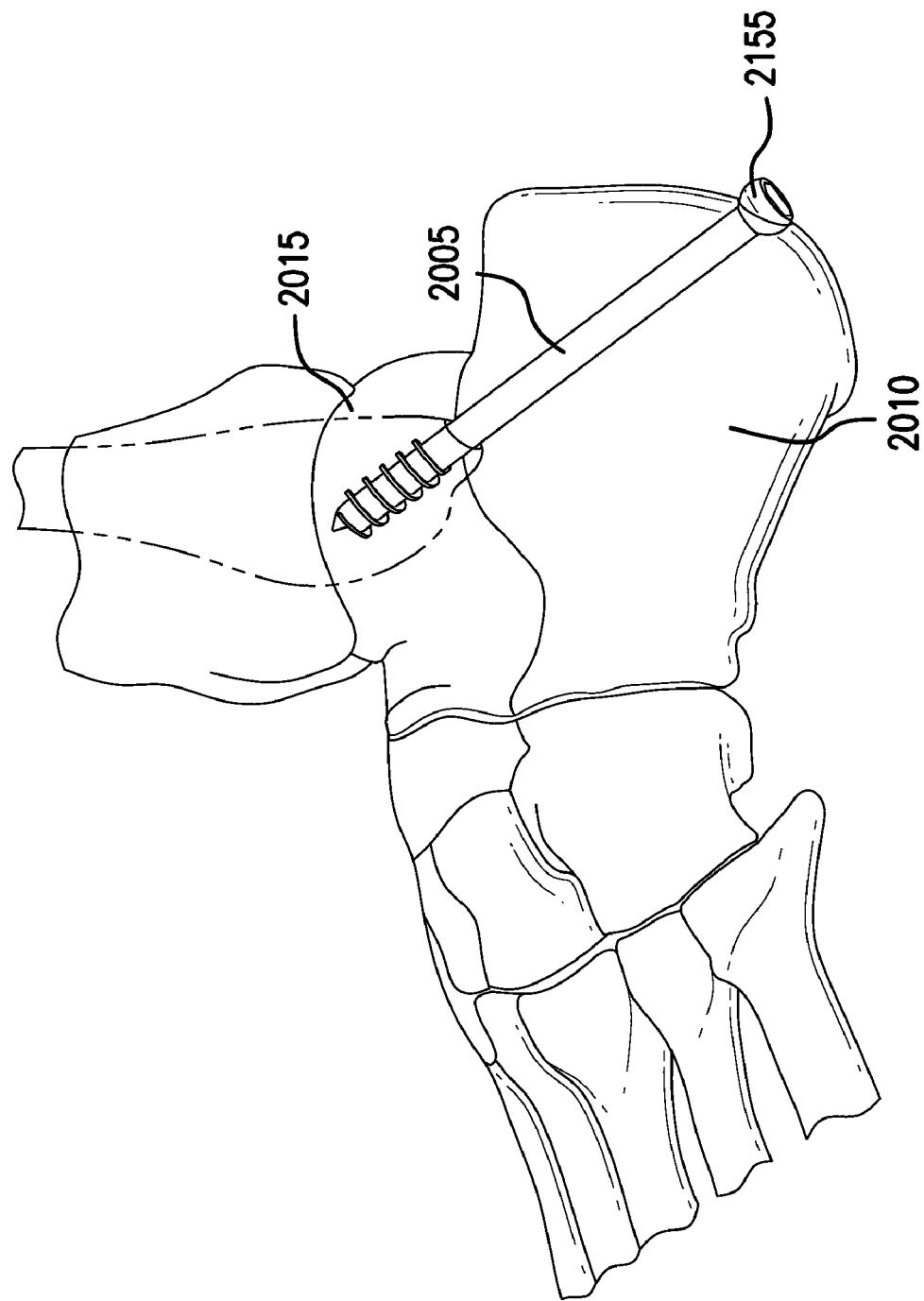
FIG. 21E a perspective image of the subtalar joint in yet another step of preparing the subtalar joint for insertion of the lag screw member of FIG. 20 according to the alternate embodiment of the invention.

In an alternate embodiment, as shown in FIG. 20, a lag screw member 2005 is provided to be utilized by, in one example, a surgeon to provide for the internal fixation of the subtalar joint comprising the calcaneus bone 2010 and talus bone 2015 bone in the skeletal system of a foot 2020. As shown, the lag screw member 2005 is substantially the same as the embodiment shown and described in FIGS. 13-16, and includes an elongated body having a threaded screw portion at one end and a tapered head 2025 at a second end, although in another embodiment, the lag screw member 2005 may be provided with a non-locking polyaxial head. The lag screw member 2005 may be cannulated or have a solid body and may be made from a Titanium material, although, in other non-limiting embodiments, the lag screw member 2005 may be made from SST, PEEK, NiTi, Cobalt chrome or other similar types of materials. It should be appreciated that the lag screw member 2005 may be provided at varying lengths for the internal fixation of a variety of bone sizes in the human body. It should also be appreciated that the lag screw member 2005 may be coated with an osteoconductive material, such as, for example, plasma spray or other similar types of porous materials that is capable of supporting or encouraging bone ingrowth into this material.

Figure 22:
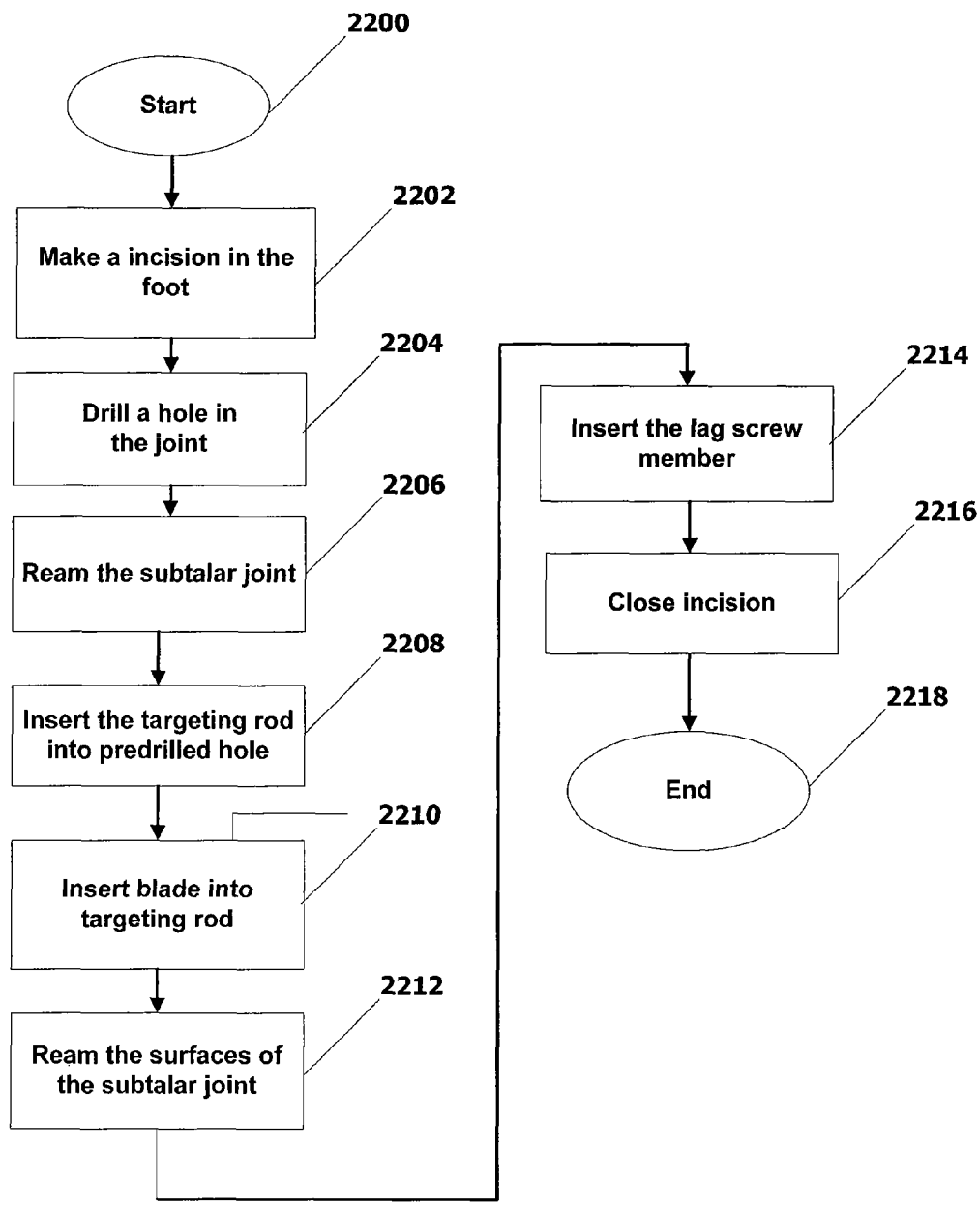
FIG. 22 is a flow chart illustrating a method of coupling the lag screw member, shown in FIG. 20, with the steps shown in FIGS. 21A-21E for fixation of the bones in a patient's foot according to the alternate embodiment of the invention.

In operation, and as shown in FIGS. 20-22, the lag screw member 2005 may be utilized to selectively apply compression to the bones of the calcaneus 2010 and the talus 2015 that form the subtalar joint (or talocalcaneal joint) of the skeletal system of foot 2020. As shown, the method starts in step 2200 and proceeds to step 2202, whereby a central incision is made in the heel area (or ventral position) of the human foot (not shown). Additionally, an anterior and posterior incision may be made in the superior portion of the human foot (not shown) to gain access to the subtalar joint, whereby cartilage on the anterior and posterior articulating surfaces of the calcaneus bone 2010 and the talus bone 2015 is removed. Next, in step 2204, a hole is pre-drilled into the calcaneus 2010 and talus 2015 bones (FIG. 21A). In this step, a cannulated drill 2100 is used to pre-drill the hole through the calcaneus 2010 and talus 2015 bones at a predetermined trajectory for insertion of the lag screw member 2005 (FIG. 20). Next, in step 2206, a reamer 2105 is inserted (FIG. 21B) into the predrilled-hole in order to prepare the joint for fusion. In this step, the head 2110 of the reamer 2105 has a blade-like structure that may be expanded and rotated inside the calcaneus 2010 and talus 2015 bones to break up the bones surrounding the pre-drilled hole. Next, in step 2208, a targeting guide assembly 2115 (FIG. 21C) may be utilized to align cutting blades with the subtalar joint in order to ream the articulating surfaces of the talus 2015 and calcaneus 2010 bones. Particularly, targeting rod 2120 is coupled to the "L-shaped" guide member 2125 and inserted into the pre-drilled hole at a predetermined depth into the calcaneus bone 2010 and the talus bone 2015. In an alternate embodiment, this depth may be varied according to the surgeon. Next, in step 2210, a percutaneous incision (not shown) is made in the side of the human foot at the location shown as indicator 2130 (FIG. 21D), and a cutting blade 2145 is inserted into the corresponding hole at the end of the rod 2120 that resides within the subtalar joint by utilizing guide member 2125. In this step, the blade 2145 is inserted by utilizing the portion 2140 on guide member 2125 to locate the axis of the blade 2145. The longitudinal axis 2135 of portion 2140 is aligned with the center of the hole in the targeting rod 2120. Next, in step 2212, the articulating surfaces of the subtalar joint is reamed by rotating the handle 2150 (FIG. 21C) causing the rotating rod 2120 to rotate and correspondingly the blade 2145 (FIG. 21D) to rotate. Once the surfaces are reamed, the blade 2145 is removed from the rod 2120 and the rod 2120 is retracted from the predrilled hole. Next, in step 2214, the lag screw member 2005 is inserted (FIG. 21E) into the predrilled hole causing it to travel into the calcaneus bone 2010 and across the subtalar joint into the talus bone 2015 until rigid connection with the surface of the calcaneus bone 2010 is made, thereby compressing the joint. It should be appreciated that the lag screw member 2005 may be inserted into the calcaneus bone 2010 until the lag screw member 2005 is flush with or slightly recessed below the cut surface of the calcaneus bone 2010. In one non-limiting embodiment, a locking element (not shown) such as a plate or a washer may be coupled to end 2155 of the lag screw member 2005 and abut tapered head 2025 to further secure the subtalar joint. Next, in step 2216, the incisions are closed. The method ends in step 2218.

It should be appreciated that the lag screw member 2005 may be inserted into any of the bones of the skeletal system of foot 2020 such as, but not limited to the metatarsal, cuneiform, calcaneus, cuboids, talus and navicular bones, in order to apply compression to the various joints in the human foot. It should also be appreciated that the lag screw member 2005 is delivered through an inferior hind-foot incision, thereby reducing the disruption to the surrounding tissues and/or the metatarsal heads while at the same time minimizing the tension on the skin. This allows for improved wound closure, reduced operating room time, reduction in the number of incisions required and reduction in the total length of incisions. It should also be appreciated that in other non-limiting embodiments, the lag screw member 2005 may be utilized with graft material (i.e., autograft, allograft or other biologic agents).

It should also be understood that this invention is not limited to the disclosed features and other similar method and system may be utilized without departing from the spirit and the scope of the invention.

While the invention has been described with reference to the preferred embodiment and alternative embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the invention is capable of being embodied in other forms without departing from its essential characteristics.

The invention claimed is:

1. A method for fusing the subtalar joint of a foot, the method comprising:
   forming a hole in the calcaneus and talus bones extending at least as far as the subtalar joint;
   reaming the hole previously formed in the calcaneus and talus bones to form a reamed hole;
   inserting a first end of an elongated rod into the reamed hole, the first end of the elongated rod having an aperture;
   making a percutaneous incision on the side of the foot;
   inserting a cutting blade through the percutaneous incision and into the aperture at the first end of the elongated rod;
   reaming an articulating surface of the calcaneus and talus bones with the cutting blade;
   inserting a screw member into the hole after reaming the articulating surface of the calcaneus and talus bones with the cutting blade; and
   applying torque to the screw member causing the screw member to compress the subtalar joint.

2. The method of claim 1 and further comprising aligning a guide member with the subtalar joint.

3. The method of claim 2, wherein the guide member comprises an elongated member having first and second ends, the first end having a first member for coupling to a second end of the elongated rod, and the second end of the elongated member having a second member extending from the elongated member.

4. The method of claim 3, wherein the second member of the elongated member extends orthogonally from the elongated member along an axis.

5. The method of claim 4 and further comprising aligning the axis of the second member of the elongated member with the aperture at the first end of the elongated rod.

6. The method of claim 3, wherein the cutting blade is inserted into the elongated rod by utilizing the second member of the guide member to insert the cutting blade into the aperture at the first end of the elongated rod.

7. The method of claim 4, wherein the guide member is aligned with the subtalar joint by coupling the elongated rod to the first member of the elongated member and by aligning the axis of the second member of the guide member with the subtalar joint.

8. The method of claim 1, wherein the screw member comprises an elongated body, a threaded portion at a first end and a bulbous portion at a second end.

9. The method of claim 8, wherein the bulbous portion includes an aperture.

10. The method of claim 9, wherein the aperture is provided to receive a complementary shaped end of an instrument.

11. The method of claim 9, wherein the aperture has a hexagonal shape, a star shape, or a square shape.

12. The method of claim 8, wherein the threaded portion comprises a plurality of bone threads disposed on an outer surface of the threaded portion.

13. The method of claim 8, wherein the threaded portion includes a self-tapping edge for removing bone material.

14. The method of claim 8, wherein the bulbous portion includes a taper for providing an interference fit with the calcaneus bone.

15. The method of claim 1 further comprising removing the elongated rod prior to inserting the screw member.

16. The method of claim 15 and further comprising removing the cutting blade from the elongated rod prior to removing the elongated rod.

17. The method of claim 1, wherein the hole is formed across the subtalar joint.

18. The method of claim 1 further comprising positioning the cutting blade laterally to a longitudinal axis of the elongated rod.

19. The method of claim 1, wherein the hole is formed in the calcaneus and talus bones using a drill.

20. The method of claim 1, wherein the hole in the calcaneus and talus bones is reamed by inserting a reamer into the hole and rotating a head member of the reamer.

21. The method of claim 1 and further comprising inserting the cutting blade in close proximity to the subtalar joint.

22. The method of claim 1 and further comprising reaming the articulating surfaces of the calcaneus and talus bones by rotating a handle connected to the elongated rod, thereby causing the cutting blade to rotate.

23. The method claim 1 and further comprising inserting the screw into the calcaneus bone across the subtalar joint and into the talus bone.

24. A method for fusing the subtalar joint of a foot, the method comprising:
   forming a hole in the calcaneus and talus bones extending at least as far as the subtalar joint;
   reaming the hole previously formed in the calcaneus and talus bones to form a reamed hole;
   inserting an elongated rod into the reamed hole formed in the calcaneus and talus bones;
   making a percutaneous incision on the side of the foot;
   aligning a targeting guide assembly with the subtalar joint, the targeting guide assembly comprising a guide member configured for coupling to the elongated rod, wherein the targeting guide assembly is aligned with the subtalar joint by aligning the guide member with the subtalar joint;
   inserting a cutting blade through the percutaneous incision and into the elongated rod previously inserted into the reamed hole;
   reaming an articulating surface of the calcaneus and talus bones with the cutting blade;
   inserting a screw member into the hole after reaming the articulating surface of the calcaneus and talus bones with the cutting blade; and
   applying torque to the screw member causing the screw member to compress the subtalar joint.

* * * * *